United States Patent
Nimer et al.

(10) Patent No.: US 9,435,809 B2
(45) Date of Patent: Sep. 6, 2016

(54) METHOD OF TREATING AND REDUCING THE RISK OF ACUTE MYELOGENOUS LEUKEMIA

(75) Inventors: Stephen D. Nimer, Miami, FL (US); Lan Wang, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 85 days.

(21) Appl. No.: 14/232,801

(22) PCT Filed: Jul. 13, 2012

(86) PCT No.: PCT/US2012/046721
§ 371 (c)(1),
(2), (4) Date: Aug. 15, 2014

(87) PCT Pub. No.: WO2013/010101
PCT Pub. Date: Jan. 17, 2013

(65) Prior Publication Data
US 2014/0348840 A1    Nov. 27, 2014

Related U.S. Application Data

(60) Provisional application No. 61/572,321, filed on Jul. 14, 2011.

(51) Int. Cl.
| | | |
|---|---|---|
| *C12Q 1/00* | (2006.01) | |
| *C12N 15/01* | (2006.01) | |
| *G01N 33/574* | (2006.01) | |
| *G01N 33/50* | (2006.01) | |
| *C07K 16/44* | (2006.01) | |
| *C12N 15/113* | (2010.01) | |
| *C12Q 1/68* | (2006.01) | |

(52) U.S. Cl.
CPC ......... *G01N 33/57426* (2013.01); *C07K 16/44* (2013.01); *C12N 15/1135* (2013.01); *C12Q 1/6886* (2013.01); *G01N 33/5011* (2013.01); *C07K 2317/34* (2013.01); *C07K 2317/40* (2013.01); *C12N 2310/14* (2013.01); *C12Q 2600/136* (2013.01); *C12Q 2600/158* (2013.01); *G01N 2440/10* (2013.01); *G01N 2500/04* (2013.01)

(58) Field of Classification Search
None
See application file for complete search history.

(56) References Cited

U.S. PATENT DOCUMENTS

| | | | | |
|---|---|---|---|---|
| 8,362,205 | B2 * | 1/2013 | Berdel | C07K 14/82 530/300 |
| 2003/0087865 | A1 * | 5/2003 | Golub et al. | 514/44 |
| 2007/0186288 | A1 | 8/2007 | Peterson et al. | |
| 2010/0303897 | A1 | 12/2010 | Jerecic | |

OTHER PUBLICATIONS

Downing et al (British Journal of Haematology, Aug. 1999, vol. 106, No. 2, pp. 296-308).*
Yamaguchi et al (Journal of Biological Chemistry, 2004, 279:15630-15638).*
Corsello et al (Blood, 2009, 113:6193-6205).*
Kitabayashi, I. et al., Interaction and functional cooperation of the leukemia-associated factors AML1 and p300 in myeloid cell differentiation, The EMBO Journal, 17(11):2994-3004 (1998).
Downing et al., The AML1-ETO Chimaeric Transcription Factor in Acute Myeloid Leukaemia: Biology and Clinical Significance, British Journal of Haematology, 106:296-308 (1999).
International Search Report for PCT/US12/46721, dated Oct. 5, 2012, published as WO 2013/010101 (3 pages).
Written Opinion for PCT/US12/46721, dated Oct. 5, 2012, published as WO 2013/010101 (12 pages).
Yan et al., Deletion of an AML1-EOT C-termination NcoR/SMRT-interacting Region Strongly Induces Leukemia Development, PNAS, 101(49):17186-17191 (2004).

\* cited by examiner

*Primary Examiner* — Laura B Goddard
(74) *Attorney, Agent, or Firm* — Choate, Hall & Stewart-LLP

(57) ABSTRACT

The present invention relates to methods and compositions for treating and reducing the risk of Acute Myelogenous Leukemia (AML). In particular, the invention provides methods for identifying novel treatments for AML based on reproducible and detectable changes in AML1-ETO acetylation. The present invention further provides methods of using these treatments.

17 Claims, 11 Drawing Sheets

A

B

| AE9a mice (week 15 Post-F.L.T.) | | | | |
|---|---|---|---|---|
| mice | AE9a | AE9aK24R | AE9aK43R | AE9aK24,43R |
| WBC(×10³/μL) | 49.6±45 | 26.8±26.3 | 7.5±1.3 * | 12.2±9.3 * |
| RBC(×M/μL) | 5.5±2.9 | 7.1±2.4 | 9.2±0.8 * | 9.4±1.1 * |
| PLT(×10³/μL) | 500.0±234.4 | 605.6±70.3 | 821.8±112.3 * | 819.2±88.5 * |

* $p<0.05$

C

D

E

SEQUENCE LISTING

<160> NUMBER OF SEQ ID NOS: 13

<210> SEQ ID NO 1
<211> LENGTH: 752
<212> TYPE: PRT
<213> ORGANISM: Homo sapiens
<220> FEATURE:
<221> NAME/KEY: ACT_SITE
<222> LOCATION: (24)..(24)
<223> OTHER INFORMATION: This site may or may not be acetylated.
<220> FEATURE:
<221> NAME/KEY: ACT_SITE
<222> LOCATION: (43)..(43)
<223> OTHER INFORMATION: This site may or may not be acetylated.

<400> SEQUENCE: 1

```
Met Arg Ile Pro Val Asp Ala Ser Thr Ser Arg Phe Thr Pro Pro
1               5                   10                  15

Ser Thr Ala Leu Ser Pro Gly Lys Met Ser Glu Ala Leu Pro Leu Gly
            20                  25                  30

Ala Pro Asp Ala Gly Ala Ala Leu Ala Gly Lys Leu Arg Ser Gly Asp
            35                  40                  45

Arg Ser Met Val Glu Val Leu Ala Asp His Pro Gly Glu Leu Val Arg
        50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
            100                 105                 110

Tyr Ser Ala Glu Leu Arg Asn Ala Thr Ala Ala Met Lys Asn Gln Val
        115                 120                 125

Ala Arg Phe Asn Asp Leu Arg Phe Val Gly Arg Ser Gly Arg Gly Lys
    130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
                165                 170                 175

Arg Asn Arg Thr Glu Lys His Ser Thr Met Pro Asp Ser Pro Val Asp
            180                 185                 190

Val Lys Thr Gln Ser Arg Leu Thr Pro Pro Thr Met Pro Pro Pro Pro
        195                 200                 205

Thr Thr Gln Gly Ala Pro Arg Thr Ser Ser Phe Thr Pro Thr Thr Leu
    210                 215                 220

Thr Asn Gly Thr Ser His Ser Pro Thr Ala Leu Asn Gly Ala Pro Ser
225                 230                 235                 240

Pro Pro Asn Gly Phe Ser Asn Gly Pro Ser Ser Ser Ser Ser Ser Ser
                245                 250                 255

Leu Ala Asn Gln Gln Leu Pro Pro Ala Cys Gly Ala Arg Gln Leu Ser
            260                 265                 270

Lys Leu Lys Arg Phe Leu Thr Thr Leu Gln Gln Phe Gly Asn Asp Ile
        275                 280                 285

Ser Pro Glu Ile Gly Glu Arg Val Arg Thr Leu Val Leu Gly Leu Val
    290                 295                 300

Asn Ser Thr Leu Thr Ile Glu Glu Phe His Ser Lys Leu Gln Glu Ala
305                 310                 315                 320
```

```
Thr Asn Phe Pro Leu Arg Pro Phe Val Ile Pro Phe Leu Lys Ala Asn
            325                 330                 335

Leu Pro Leu Leu Gln Arg Glu Leu Leu His Cys Ala Arg Leu Ala Lys
        340                 345                 350

Gln Asn Pro Ala Gln Tyr Leu Ala Gln His Glu Gln Leu Leu Leu Asp
        355                 360                 365

Ala Ser Thr Thr Ser Pro Val Asp Ser Ser Glu Leu Leu Leu Asp Val
370                 375                 380

Asn Glu Asn Gly Lys Arg Arg Thr Pro Asp Arg Thr Lys Glu Asn Gly
385                 390                 395                 400

Phe Asp Arg Glu Pro Leu His Ser Glu His Pro Ser Lys Arg Pro Cys
                405                 410                 415

Thr Ile Ser Pro Gly Gln Arg Tyr Ser Pro Asn Asn Gly Leu Ser Tyr
            420                 425                 430

Gln Pro Asn Gly Leu Pro His Pro Thr Pro Pro Pro Gln His Tyr
        435                 440                 445

Arg Leu Asp Asp Met Ala Ile Ala His His Tyr Arg Asp Ser Tyr Arg
    450                 455                 460

His Pro Ser His Arg Asp Leu Arg Asp Arg Asn Arg Pro Met Gly Leu
465                 470                 475                 480

His Gly Thr Arg Gln Glu Glu Met Ile Asp His Arg Leu Thr Asp Arg
                485                 490                 495

Glu Trp Ala Glu Glu Trp Lys His Leu Asp His Leu Leu Asn Cys Ile
                500                 505                 510

Met Asp Met Val Glu Lys Thr Arg Arg Ser Leu Thr Val Leu Arg Arg
            515                 520                 525

Cys Gln Glu Ala Asp Arg Glu Glu Leu Asn Tyr Trp Ile Arg Arg Tyr
        530                 535                 540

Ser Asp Ala Glu Asp Leu Lys Lys Gly Gly Gly Ser Ser Ser Ser His
545                 550                 555                 560

Ser Arg Gln Gln Ser Pro Val Asn Pro Asp Pro Val Ala Leu Asp Ala
                565                 570                 575

His Arg Glu Phe Leu His Arg Pro Ala Ser Gly Tyr Val Pro Glu Glu
            580                 585                 590

Ile Trp Lys Lys Ala Glu Glu Ala Val Asn Glu Val Lys Arg Gln Ala
        595                 600                 605

Met Thr Glu Leu Gln Lys Ala Val Ser Glu Ala Glu Arg Lys Ala His
    610                 615                 620

Asp Met Ile Thr Thr Glu Arg Ala Lys Met Glu Arg Thr Val Ala Glu
625                 630                 635                 640

Ala Lys Arg Gln Ala Ala Glu Asp Ala Leu Ala Val Ile Asn Gln Gln
                645                 650                 655

Glu Asp Ser Ser Glu Ser Cys Trp Asn Cys Gly Arg Lys Ala Ser Glu
            660                 665                 670

Thr Cys Ser Gly Cys Asn Thr Ala Arg Tyr Cys Gly Ser Phe Cys Gln
        675                 680                 685

His Lys Asp Trp Glu Lys His His Ile Cys Gly Gln Thr Leu Gln
    690                 695                 700

Ala Gln Gln Gln Gly Asp Thr Pro Ala Val Ser Ser Ser Val Thr Pro
705                 710                 715                 720

Asn Ser Gly Ala Gly Ser Pro Met Asp Thr Pro Pro Ala Ala Thr Pro
                725                 730                 735
```

-continued

Arg Ser Thr Thr Pro Gly Thr Pro Ser Thr Ile Glu Thr Pro Arg
                740             745             750

<210> SEQ ID NO 2
<211> LENGTH: 531
<212> TYPE: PRT
<213> ORGANISM: Artificial Sequence
<220> FEATURE:
<223> OTHER INFORMATION: Human AML1-ETO delta NHR1

<400> SEQUENCE: 2

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
            20                  25                  30

Ala Pro Asp Ala Gly Ala Ala Leu Ala Gly Lys Leu Arg Ser Gly Asp
        35                  40                  45

Arg Ser Met Val Glu Val Leu Ala Asp His Pro Gly Glu Leu Val Arg
    50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
            100                 105                 110

Tyr Ser Ala Glu Leu Arg Asn Ala Thr Ala Ala Met Lys Asn Gln Val
        115                 120                 125

Ala Arg Phe Asn Asp Leu Arg Phe Val Gly Arg Ser Gly Arg Gly Lys
    130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
                165                 170                 175

Arg Asn Arg Thr Glu Lys His Ser Thr Met Pro Asp Ser Pro Val Asp
            180                 185                 190

Val Lys Thr Gln Ser Arg Leu Thr Pro Pro Thr Met Pro Pro Pro Pro
        195                 200                 205

Thr Thr Gln Gly Ala Pro Arg Thr Ser Ser Phe Thr Pro Thr Thr Leu
    210                 215                 220

Thr Asn Gly Thr Ser His Ser Pro Thr Ala Leu Asn Gly Ala Pro Ser
225                 230                 235                 240

Pro Pro Asn Gly Phe Ser His Arg Asp Leu Arg Asp Arg Asn Arg Pro
                245                 250                 255

Met Gly Leu His Gly Thr Arg Gln Glu Glu Met Ile Asp His Arg Leu
            260                 265                 270

Thr Asp Arg Glu Trp Ala Glu Glu Trp Lys His Leu Asp His Leu Leu
        275                 280                 285

Asn Cys Ile Met Asp Met Val Glu Lys Thr Arg Arg Ser Leu Thr Val
    290                 295                 300

Leu Arg Arg Cys Gln Glu Ala Asp Arg Glu Glu Leu Asn Tyr Trp Ile
305                 310                 315                 320

Arg Arg Tyr Ser Asp Ala Glu Asp Leu Lys Lys Gly Gly Gly Ser Ser
                325                 330                 335

Ser Ser His Ser Arg Gln Gln Ser Pro Val Asn Pro Asp Pro Val Ala
            340                 345                 350

Leu Asp Ala His Arg Glu Phe Leu His Arg Pro Ala Ser Gly Tyr Val
            355                 360                 365

Pro Glu Glu Ile Trp Lys Lys Ala Glu Ala Val Asn Glu Val Lys
    370                 375                 380

Arg Gln Ala Met Thr Glu Leu Gln Lys Ala Val Ser Glu Ala Glu Arg
385                 390                 395                 400

Lys Ala His Asp Met Ile Thr Thr Glu Arg Ala Lys Met Glu Arg Thr
                405                 410                 415

Val Ala Glu Ala Lys Arg Gln Ala Ala Glu Asp Ala Leu Ala Val Ile
                420                 425                 430

Asn Gln Gln Glu Asp Ser Ser Glu Ser Cys Trp Asn Cys Gly Arg Lys
            435                 440                 445

Ala Ser Glu Thr Cys Ser Gly Cys Asn Thr Ala Arg Tyr Cys Gly Ser
    450                 455                 460

Phe Cys Gln His Lys Asp Trp Glu Lys His His His Ile Cys Gly Gln
465                 470                 475                 480

Thr Leu Gln Ala Gln Gln Gln Gly Asp Thr Pro Ala Val Ser Ser Ser
                485                 490                 495

Val Thr Pro Asn Ser Gly Ala Gly Ser Pro Met Asp Thr Pro Pro Ala
            500                 505                 510

Ala Thr Pro Arg Ser Thr Thr Pro Gly Thr Pro Ser Thr Ile Glu Thr
    515                 520                 525

Thr Pro Arg
    530

<210> SEQ ID NO 3
<211> LENGTH: 685
<212> TYPE: PRT
<213> ORGANISM: Artificial Sequence
<220> FEATURE:
<223> OTHER INFORMATION: Human AML1-ETO delta NHR2

<400> SEQUENCE: 3

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
            20                  25                  30

Ala Pro Asp Ala Gly Ala Ala Leu Ala Gly Lys Leu Arg Ser Gly Asp
        35                  40                  45

Arg Ser Met Val Glu Val Leu Ala Asp His Pro Gly Glu Leu Val Arg
    50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
            100                 105                 110

Tyr Ser Ala Glu Leu Arg Asn Ala Thr Ala Ala Met Lys Asn Gln Val
        115                 120                 125

Ala Arg Phe Asn Asp Leu Arg Phe Val Gly Arg Ser Gly Arg Gly Lys
    130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
                165                 170                 175

-continued

```
Arg Asn Arg Thr Glu Lys His Ser Thr Met Pro Asp Ser Pro Val Asp
            180                 185                 190
Val Lys Thr Gln Ser Arg Leu Thr Pro Pro Thr Met Pro Pro Pro Pro
        195                 200                 205
Thr Thr Gln Gly Ala Pro Arg Thr Ser Ser Phe Thr Pro Thr Thr Leu
    210                 215                 220
Thr Asn Gly Thr Ser His Ser Pro Thr Ala Leu Asn Gly Ala Pro Ser
225                 230                 235                 240
Pro Pro Asn Gly Phe Ser Asn Gly Pro Ser Ser Ser Ser Ser Ser Ser
                245                 250                 255
Leu Ala Asn Gln Gln Leu Pro Pro Ala Cys Gly Ala Arg Gln Leu Ser
            260                 265                 270
Lys Leu Lys Arg Phe Leu Thr Thr Leu Gln Gln Phe Gly Asn Asp Ile
        275                 280                 285
Ser Pro Glu Ile Gly Glu Arg Val Arg Thr Leu Val Leu Gly Leu Val
    290                 295                 300
Asn Ser Thr Leu Thr Ile Glu Glu Phe His Ser Lys Leu Gln Glu Ala
305                 310                 315                 320
Thr Asn Phe Pro Leu Arg Pro Phe Val Ile Pro Phe Leu Lys Ala Asn
                325                 330                 335
Leu Pro Leu Leu Gln Arg Glu Leu Leu His Cys Ala Arg Leu Ala Lys
            340                 345                 350
Gln Asn Pro Ala Gln Tyr Leu Ala Gln His Glu Gln Leu Leu Leu Asp
        355                 360                 365
Ala Ser Thr Thr Ser Pro Val Asp Ser Ser Glu Leu Leu Leu Asp Val
    370                 375                 380
Asn Glu Asn Gly Lys Arg Arg Thr Pro Asp Arg Thr Lys Glu Asn Gly
385                 390                 395                 400
Phe Asp Arg Glu Pro Leu His Ser Glu His Pro Ser Lys Arg Pro Cys
                405                 410                 415
Thr Ile Ser Pro Gly Gln Arg Tyr Ser Pro Asn Asn Gly Leu Ser Tyr
            420                 425                 430
Gln Pro Asn Gly Leu Pro His Pro Thr Pro Pro Pro Gln His Tyr
        435                 440                 445
Arg Leu Asp Asp Met Ala Ile Ala His His Tyr Arg Asp Ser Tyr Arg
    450                 455                 460
His Pro Ser His Arg Asp Leu Arg Asp Arg Asn Arg Pro Met Gly Leu
465                 470                 475                 480
Glu Asp Leu Lys Lys Gly Gly Ser Ser Ser His Ser Arg Gln
                485                 490                 495
Gln Ser Pro Val Asn Pro Asp Pro Val Ala Leu Asp Ala His Arg Glu
            500                 505                 510
Phe Leu His Arg Pro Ala Ser Gly Tyr Val Pro Glu Glu Ile Trp Lys
        515                 520                 525
Lys Ala Glu Glu Ala Val Asn Glu Val Lys Arg Gln Ala Met Thr Glu
    530                 535                 540
Leu Gln Lys Ala Val Ser Glu Ala Glu Arg Lys Ala His Asp Met Ile
545                 550                 555                 560
Thr Thr Glu Arg Ala Lys Met Glu Arg Thr Val Ala Glu Ala Lys Arg
                565                 570                 575
Gln Ala Ala Glu Asp Ala Leu Ala Val Ile Asn Gln Gln Glu Asp Ser
            580                 585                 590
```

```
Ser Glu Ser Cys Trp Asn Cys Gly Arg Lys Ala Ser Glu Thr Cys Ser
            595                 600                 605

Gly Cys Asn Thr Ala Arg Tyr Cys Gly Ser Phe Cys Gln His Lys Asp
610                 615                 620

Trp Glu Lys His His His Ile Cys Gly Gln Thr Leu Gln Ala Gln Gln
625                 630                 635                 640

Gln Gly Asp Thr Pro Ala Val Ser Ser Val Thr Pro Asn Ser Gly
            645                 650                 655

Ala Gly Ser Pro Met Asp Thr Pro Ala Ala Thr Pro Arg Ser Thr
            660                 665                 670

Thr Pro Gly Thr Pro Ser Thr Ile Glu Thr Thr Pro Arg
            675                 680                 685

<210> SEQ ID NO 4
<211> LENGTH: 619
<212> TYPE: PRT
<213> ORGANISM: Artificial Sequence
<220> FEATURE:
<223> OTHER INFORMATION: Human AML1-ETO delta Runt

<400> SEQUENCE: 4

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
            20                  25                  30

Ala Pro Asp Ala Gly Ala Ala Leu Ala Gly Lys Leu Arg Ser Gly Asp
        35                  40                  45

Lys His Ser Thr Met Pro Asp Ser Pro Val Asp Val Lys Thr Gln Ser
    50                  55                  60

Arg Leu Thr Pro Pro Thr Met Pro Pro Pro Thr Thr Gln Gly Ala
65                  70                  75                  80

Pro Arg Thr Ser Ser Phe Thr Pro Thr Thr Leu Thr Asn Gly Thr Ser
                85                  90                  95

His Ser Pro Thr Ala Leu Asn Gly Ala Pro Ser Pro Pro Asn Gly Phe
            100                 105                 110

Ser Asn Gly Pro Ser Ser Ser Ser Ser Ser Leu Ala Asn Gln Gln
        115                 120                 125

Leu Pro Pro Ala Cys Gly Ala Arg Gln Leu Ser Lys Leu Lys Arg Phe
130                 135                 140

Leu Thr Thr Leu Gln Gln Phe Gly Asn Asp Ile Ser Pro Glu Ile Gly
145                 150                 155                 160

Glu Arg Val Arg Thr Leu Val Leu Gly Leu Val Asn Ser Thr Leu Thr
                165                 170                 175

Ile Glu Glu Phe His Ser Lys Leu Gln Glu Ala Thr Asn Phe Pro Leu
            180                 185                 190

Arg Pro Phe Val Ile Pro Phe Leu Lys Ala Asn Leu Pro Leu Leu Gln
        195                 200                 205

Arg Glu Leu Leu His Cys Ala Arg Leu Ala Lys Gln Asn Pro Ala Gln
    210                 215                 220

Tyr Leu Ala Gln His Glu Gln Leu Leu Leu Asp Ala Ser Thr Thr Ser
225                 230                 235                 240

Pro Val Asp Ser Ser Glu Leu Leu Leu Asp Val Asn Glu Asn Gly Lys
                245                 250                 255

Arg Arg Thr Pro Asp Arg Thr Lys Glu Asn Gly Phe Asp Arg Glu Pro
            260                 265                 270
```

```
Leu His Ser Glu His Pro Ser Lys Arg Pro Cys Thr Ile Ser Pro Gly
            275                 280                 285

Gln Arg Tyr Ser Pro Asn Asn Gly Leu Ser Tyr Gln Pro Asn Gly Leu
290                 295                 300

Pro His Pro Thr Pro Pro Pro Gln His Tyr Arg Leu Asp Asp Met
305                 310                 315                 320

Ala Ile Ala His His Tyr Arg Asp Ser Tyr Arg His Pro Ser His Arg
            325                 330                 335

Asp Leu Arg Asp Arg Asn Arg Pro Met Gly Leu His Gly Thr Arg Gln
            340                 345                 350

Glu Glu Met Ile Asp His Arg Leu Thr Asp Arg Glu Trp Ala Glu Glu
            355                 360                 365

Trp Lys His Leu Asp His Leu Leu Asn Cys Ile Met Asp Met Val Glu
            370                 375                 380

Lys Thr Arg Arg Ser Leu Thr Val Leu Arg Arg Cys Gln Glu Ala Asp
385                 390                 395                 400

Arg Glu Glu Leu Asn Tyr Trp Ile Arg Arg Tyr Ser Asp Ala Glu Asp
            405                 410                 415

Leu Lys Lys Gly Gly Gly Ser Ser Ser His Ser Arg Gln Gln Ser
            420                 425                 430

Pro Val Asn Pro Asp Pro Val Ala Leu Asp Ala His Arg Glu Phe Leu
            435                 440                 445

His Arg Pro Ala Ser Gly Tyr Val Pro Glu Glu Ile Trp Lys Lys Ala
            450                 455                 460

Glu Glu Ala Val Asn Glu Val Lys Arg Gln Ala Met Thr Glu Leu Gln
465                 470                 475                 480

Lys Ala Val Ser Glu Ala Glu Arg Lys Ala His Asp Met Ile Thr Thr
            485                 490                 495

Glu Arg Ala Lys Met Glu Arg Thr Val Ala Glu Ala Lys Arg Gln Ala
            500                 505                 510

Ala Glu Asp Ala Leu Ala Val Ile Asn Gln Gln Glu Asp Ser Ser Glu
            515                 520                 525

Ser Cys Trp Asn Cys Gly Arg Lys Ala Ser Glu Thr Cys Ser Gly Cys
530                 535                 540

Asn Thr Ala Arg Tyr Cys Gly Ser Phe Cys Gln His Lys Asp Trp Glu
545                 550                 555                 560

Lys His His His Ile Cys Gly Gln Thr Leu Gln Ala Gln Gln Gln Gly
            565                 570                 575

Asp Thr Pro Ala Val Ser Ser Ser Val Thr Pro Asn Ser Gly Ala Gly
            580                 585                 590

Ser Pro Met Asp Thr Pro Pro Ala Ala Thr Pro Arg Ser Thr Thr Pro
            595                 600                 605

Gly Thr Pro Ser Thr Ile Glu Thr Thr Pro Arg
            610                 615

<210> SEQ ID NO 5
<211> LENGTH: 752
<212> TYPE: PRT
<213> ORGANISM: Artificial Sequence
<220> FEATURE:
<223> OTHER INFORMATION: Human AML1-ETO K24R

<400> SEQUENCE: 5

Met Arg Ile Pro Val Asp Ala Ser Thr Ser Arg Arg Phe Thr Pro Pro
1               5                   10                  15
```

```
Ser Thr Ala Leu Ser Pro Gly Arg Met Ser Glu Ala Leu Pro Leu Gly
            20                  25                  30

Ala Pro Asp Ala Gly Ala Ala Leu Ala Gly Lys Leu Arg Ser Gly Asp
            35                  40                  45

Arg Ser Met Val Glu Val Leu Ala Asp His Pro Gly Glu Leu Val Arg
            50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
            100                 105                 110

Tyr Ser Ala Glu Leu Arg Asn Ala Thr Ala Ala Met Lys Asn Gln Val
            115                 120                 125

Ala Arg Phe Asn Asp Leu Arg Phe Val Gly Arg Ser Gly Arg Gly Lys
            130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
            165                 170                 175

Arg Asn Arg Thr Glu Lys His Ser Thr Met Pro Asp Ser Pro Val Asp
            180                 185                 190

Val Lys Thr Gln Ser Arg Leu Thr Pro Pro Thr Met Pro Pro Pro Pro
            195                 200                 205

Thr Thr Gln Gly Ala Pro Arg Thr Ser Ser Phe Thr Pro Thr Thr Leu
            210                 215                 220

Thr Asn Gly Thr Ser His Ser Pro Thr Ala Leu Asn Gly Ala Pro Ser
225                 230                 235                 240

Pro Pro Asn Gly Phe Ser Asn Gly Pro Ser Ser Ser Ser Ser Ser Ser
                245                 250                 255

Leu Ala Asn Gln Gln Leu Pro Pro Ala Cys Gly Ala Arg Gln Leu Ser
            260                 265                 270

Lys Leu Lys Arg Phe Leu Thr Thr Leu Gln Gln Phe Gly Asn Asp Ile
            275                 280                 285

Ser Pro Glu Ile Gly Glu Arg Val Arg Thr Leu Val Leu Gly Leu Val
            290                 295                 300

Asn Ser Thr Leu Thr Ile Glu Glu Phe His Ser Lys Leu Gln Glu Ala
305                 310                 315                 320

Thr Asn Phe Pro Leu Arg Pro Phe Val Ile Pro Phe Leu Lys Ala Asn
            325                 330                 335

Leu Pro Leu Leu Gln Arg Glu Leu Leu His Cys Ala Arg Leu Ala Lys
            340                 345                 350

Gln Asn Pro Ala Gln Tyr Leu Ala Gln His Glu Gln Leu Leu Leu Asp
            355                 360                 365

Ala Ser Thr Thr Ser Pro Val Asp Ser Ser Glu Leu Leu Leu Asp Val
            370                 375                 380

Asn Glu Asn Gly Lys Arg Arg Thr Pro Asp Arg Thr Lys Glu Asn Gly
385                 390                 395                 400

Phe Asp Arg Glu Pro Leu His Ser Glu His Pro Ser Lys Arg Pro Cys
            405                 410                 415

Thr Ile Ser Pro Gly Gln Arg Tyr Ser Pro Asn Asn Gly Leu Ser Tyr
            420                 425                 430
```

```
Gln Pro Asn Gly Leu Pro His Pro Thr Pro Pro Pro Gln His Tyr
            435                 440                 445

Arg Leu Asp Asp Met Ala Ile Ala His His Tyr Arg Asp Ser Tyr Arg
450                 455                 460

His Pro Ser His Arg Asp Leu Arg Asp Arg Asn Arg Pro Met Gly Leu
465                 470                 475                 480

His Gly Thr Arg Gln Glu Glu Met Ile Asp His Arg Leu Thr Asp Arg
                485                 490                 495

Glu Trp Ala Glu Glu Trp Lys His Leu Asp His Leu Leu Asn Cys Ile
            500                 505                 510

Met Asp Met Val Glu Lys Thr Arg Arg Ser Leu Thr Val Leu Arg Arg
        515                 520                 525

Cys Gln Glu Ala Asp Arg Glu Glu Leu Asn Tyr Trp Ile Arg Arg Tyr
    530                 535                 540

Ser Asp Ala Glu Asp Leu Lys Lys Gly Gly Gly Ser Ser Ser Ser His
545                 550                 555                 560

Ser Arg Gln Gln Ser Pro Val Asn Pro Asp Pro Val Ala Leu Asp Ala
                565                 570                 575

His Arg Glu Phe Leu His Arg Pro Ala Ser Gly Tyr Val Pro Glu Glu
            580                 585                 590

Ile Trp Lys Lys Ala Glu Glu Ala Val Asn Glu Val Lys Arg Gln Ala
        595                 600                 605

Met Thr Glu Leu Gln Lys Ala Val Ser Glu Ala Glu Arg Lys Ala His
    610                 615                 620

Asp Met Ile Thr Thr Glu Arg Ala Lys Met Glu Arg Thr Val Ala Glu
625                 630                 635                 640

Ala Lys Arg Gln Ala Ala Glu Asp Ala Leu Ala Val Ile Asn Gln Gln
                645                 650                 655

Glu Asp Ser Ser Glu Ser Cys Trp Asn Cys Gly Arg Lys Ala Ser Glu
            660                 665                 670

Thr Cys Ser Gly Cys Asn Thr Ala Arg Tyr Cys Gly Ser Phe Cys Gln
    675                 680                 685

His Lys Asp Trp Glu Lys His His His Ile Cys Gly Gln Thr Leu Gln
690                 695                 700

Ala Gln Gln Gln Gly Asp Thr Pro Ala Val Ser Ser Val Thr Pro
705                 710                 715                 720

Asn Ser Gly Ala Gly Ser Pro Met Asp Thr Pro Ala Ala Thr Pro
                725                 730                 735

Arg Ser Thr Thr Pro Gly Thr Pro Ser Thr Ile Glu Thr Thr Pro Arg
            740                 745                 750

<210> SEQ ID NO 6
<211> LENGTH: 752
<212> TYPE: PRT
<213> ORGANISM: Artificial Sequence
<220> FEATURE:
<223> OTHER INFORMATION: Human AML1-ETO K43R

<400> SEQUENCE: 6

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
            20                  25                  30

Ala Pro Asp Ala Gly Ala Ala Leu Ala Gly Arg Leu Arg Ser Gly Asp
        35                  40                  45
```

```
Arg Ser Met Val Glu Val Leu Ala Asp His Pro Gly Glu Leu Val Arg
    50              55                  60
Thr Asp Ser Pro Asn Phe Leu Cys Ser Val Leu Pro Thr His Trp Arg
65              70                  75                  80
Cys Asn Lys Thr Leu Pro Ile Ala Phe Lys Val Val Ala Leu Gly Asp
                85                  90                  95
Val Pro Asp Gly Thr Leu Val Thr Val Met Ala Gly Asn Asp Glu Asn
                100                 105                 110
Tyr Ser Ala Glu Leu Arg Asn Ala Thr Ala Met Lys Asn Gln Val
                115                 120                 125
Ala Arg Phe Asn Asp Leu Arg Phe Val Gly Arg Ser Gly Arg Gly Lys
    130                 135                 140
Ser Phe Thr Leu Thr Ile Thr Val Phe Thr Asn Pro Pro Gln Val Ala
145                 150                 155                 160
Thr Tyr His Arg Ala Ile Lys Ile Thr Val Asp Gly Pro Arg Glu Pro
                165                 170                 175
Arg Asn Arg Thr Glu Lys His Ser Thr Met Pro Asp Ser Pro Val Asp
                180                 185                 190
Val Lys Thr Gln Ser Arg Leu Thr Pro Pro Thr Met Pro Pro Pro
    195                 200                 205
Thr Thr Gln Gly Ala Pro Arg Thr Ser Ser Phe Thr Pro Thr Thr Leu
    210                 215                 220
Thr Asn Gly Thr Ser His Ser Pro Thr Ala Leu Asn Gly Ala Pro Ser
225                 230                 235                 240
Pro Pro Asn Gly Phe Ser Asn Gly Pro Ser Ser Ser Ser Ser Ser
                245                 250                 255
Leu Ala Asn Gln Gln Leu Pro Ala Cys Gly Ala Arg Gln Leu Ser
    260                 265                 270
Lys Leu Lys Arg Phe Leu Thr Thr Leu Gln Gln Phe Gly Asn Asp Ile
    275                 280                 285
Ser Pro Glu Ile Gly Glu Arg Val Arg Thr Leu Val Leu Gly Leu Val
    290                 295                 300
Asn Ser Thr Leu Thr Ile Glu Glu Phe His Ser Lys Leu Gln Glu Ala
305                 310                 315                 320
Thr Asn Phe Pro Leu Arg Pro Phe Val Ile Pro Phe Leu Lys Ala Asn
                325                 330                 335
Leu Pro Leu Leu Gln Arg Glu Leu Leu His Cys Ala Arg Leu Ala Lys
                340                 345                 350
Gln Asn Pro Ala Gln Tyr Leu Ala Gln His Glu Gln Leu Leu Leu Asp
    355                 360                 365
Ala Ser Thr Thr Ser Pro Val Asp Ser Ser Glu Leu Leu Leu Asp Val
    370                 375                 380
Asn Glu Asn Gly Lys Arg Arg Thr Pro Asp Arg Thr Lys Glu Asn Gly
385                 390                 395                 400
Phe Asp Arg Glu Pro Leu His Ser Glu His Pro Ser Lys Arg Pro Cys
                405                 410                 415
Thr Ile Ser Pro Gly Gln Arg Tyr Ser Pro Asn Asn Gly Leu Ser Tyr
                420                 425                 430
Gln Pro Asn Gly Leu Pro His Pro Thr Pro Pro Pro Gln His Tyr
    435                 440                 445
Arg Leu Asp Asp Met Ala Ile Ala His His Tyr Arg Asp Ser Tyr Arg
    450                 455                 460
```

-continued

```
His Pro Ser His Arg Asp Leu Arg Asp Arg Asn Arg Pro Met Gly Leu
465                 470                 475                 480

His Gly Thr Arg Gln Glu Glu Met Ile Asp His Arg Leu Thr Asp Arg
            485                 490                 495

Glu Trp Ala Glu Glu Trp Lys His Leu Asp His Leu Leu Asn Cys Ile
        500                 505                 510

Met Asp Met Val Glu Lys Thr Arg Arg Ser Leu Thr Val Leu Arg Arg
    515                 520                 525

Cys Gln Glu Ala Asp Arg Glu Glu Leu Asn Tyr Trp Ile Arg Arg Tyr
530                 535                 540

Ser Asp Ala Glu Asp Leu Lys Lys Gly Gly Gly Ser Ser Ser Ser His
545                 550                 555                 560

Ser Arg Gln Gln Ser Pro Val Asn Pro Asp Pro Val Ala Leu Asp Ala
            565                 570                 575

His Arg Glu Phe Leu His Arg Pro Ala Ser Gly Tyr Val Pro Glu Glu
        580                 585                 590

Ile Trp Lys Lys Ala Glu Glu Ala Val Asn Glu Val Lys Arg Gln Ala
    595                 600                 605

Met Thr Glu Leu Gln Lys Ala Val Ser Glu Ala Glu Arg Lys Ala His
610                 615                 620

Asp Met Ile Thr Thr Glu Arg Ala Lys Met Glu Arg Thr Val Ala Glu
625                 630                 635                 640

Ala Lys Arg Gln Ala Ala Glu Asp Ala Leu Ala Val Ile Asn Gln Gln
            645                 650                 655

Glu Asp Ser Ser Glu Ser Cys Trp Asn Cys Gly Arg Lys Ala Ser Glu
        660                 665                 670

Thr Cys Ser Gly Cys Asn Thr Ala Arg Tyr Cys Gly Ser Phe Cys Gln
    675                 680                 685

His Lys Asp Trp Glu Lys His His His Ile Cys Gly Gln Thr Leu Gln
690                 695                 700

Ala Gln Gln Gln Gly Asp Thr Pro Ala Val Ser Ser Ser Val Thr Pro
705                 710                 715                 720

Asn Ser Gly Ala Gly Ser Pro Met Asp Thr Pro Ala Ala Thr Pro
            725                 730                 735

Arg Ser Thr Thr Pro Gly Thr Pro Ser Thr Ile Glu Thr Thr Pro Arg
            740                 745                 750

<210> SEQ ID NO 7
<211> LENGTH: 752
<212> TYPE: PRT
<213> ORGANISM: Artificial Sequence
<220> FEATURE:
<223> OTHER INFORMATION: Human AML1-ETO K24R K43R

<400> SEQUENCE: 7

Met Arg Ile Pro Val Asp Ala Ser Thr Ser Arg Arg Phe Thr Pro Pro
1               5                   10                  15

Ser Thr Ala Leu Ser Pro Gly Arg Met Ser Glu Ala Leu Pro Leu Gly
            20                  25                  30

Ala Pro Asp Ala Gly Ala Ala Leu Ala Gly Arg Leu Arg Ser Gly Asp
        35                  40                  45

Arg Ser Met Val Glu Val Leu Ala Asp His Pro Gly Glu Leu Val Arg
    50                  55                  60

Thr Asp Ser Pro Asn Phe Leu Cys Ser Val Leu Pro Thr His Trp Arg
65                  70                  75                  80
```

```
Cys Asn Lys Thr Leu Pro Ile Ala Phe Lys Val Val Ala Leu Gly Asp
                85                  90                  95
Val Pro Asp Gly Thr Leu Val Thr Val Met Ala Gly Asn Asp Glu Asn
            100                 105                 110
Tyr Ser Ala Glu Leu Arg Asn Ala Thr Ala Ala Met Lys Asn Gln Val
        115                 120                 125
Ala Arg Phe Asn Asp Leu Arg Phe Val Gly Arg Ser Gly Arg Gly Lys
    130                 135                 140
Ser Phe Thr Leu Thr Ile Thr Val Phe Thr Asn Pro Pro Gln Val Ala
145                 150                 155                 160
Thr Tyr His Arg Ala Ile Lys Ile Thr Val Asp Gly Pro Arg Glu Pro
                165                 170                 175
Arg Asn Arg Thr Glu Lys His Ser Thr Met Pro Asp Ser Pro Val Asp
            180                 185                 190
Val Lys Thr Gln Ser Arg Leu Thr Pro Pro Thr Met Pro Pro Pro Pro
        195                 200                 205
Thr Thr Gln Gly Ala Pro Arg Thr Ser Ser Phe Thr Pro Thr Thr Leu
    210                 215                 220
Thr Asn Gly Thr Ser His Ser Pro Thr Ala Leu Asn Gly Ala Pro Ser
225                 230                 235                 240
Pro Pro Asn Gly Phe Ser Asn Gly Pro Ser Ser Ser Ser Ser Ser Ser
                245                 250                 255
Leu Ala Asn Gln Gln Leu Pro Pro Ala Cys Gly Ala Arg Gln Leu Ser
            260                 265                 270
Lys Leu Lys Arg Phe Leu Thr Thr Leu Gln Gln Phe Gly Asn Asp Ile
        275                 280                 285
Ser Pro Glu Ile Gly Glu Arg Val Arg Thr Leu Val Leu Gly Leu Val
    290                 295                 300
Asn Ser Thr Leu Thr Ile Glu Glu Phe His Ser Lys Leu Gln Glu Ala
305                 310                 315                 320
Thr Asn Phe Pro Leu Arg Pro Phe Val Ile Pro Phe Leu Lys Ala Asn
                325                 330                 335
Leu Pro Leu Leu Gln Arg Glu Leu Leu His Cys Ala Arg Leu Ala Lys
            340                 345                 350
Gln Asn Pro Ala Gln Tyr Leu Ala Gln His Glu Gln Leu Leu Leu Asp
        355                 360                 365
Ala Ser Thr Thr Ser Pro Val Asp Ser Ser Glu Leu Leu Leu Asp Val
    370                 375                 380
Asn Glu Asn Gly Lys Arg Arg Thr Pro Asp Arg Thr Lys Glu Asn Gly
385                 390                 395                 400
Phe Asp Arg Glu Pro Leu His Ser Glu His Pro Ser Lys Arg Pro Cys
                405                 410                 415
Thr Ile Ser Pro Gly Gln Arg Tyr Ser Pro Asn Asn Gly Leu Ser Tyr
            420                 425                 430
Gln Pro Asn Gly Leu Pro His Pro Thr Pro Pro Pro Gln His Tyr
        435                 440                 445
Arg Leu Asp Asp Met Ala Ile Ala His His Tyr Arg Asp Ser Tyr Arg
    450                 455                 460
His Pro Ser His Arg Asp Leu Arg Asp Arg Asn Arg Pro Met Gly Leu
465                 470                 475                 480
His Gly Thr Arg Gln Glu Glu Met Ile Asp His Arg Leu Thr Asp Arg
                485                 490                 495
```

```
Glu Trp Ala Glu Trp Lys His Leu Asp His Leu Leu Asn Cys Ile
                500                 505                 510

Met Asp Met Val Glu Lys Thr Arg Arg Ser Leu Thr Val Leu Arg Arg
            515                 520                 525

Cys Gln Glu Ala Asp Arg Glu Glu Leu Asn Tyr Trp Ile Arg Arg Tyr
        530                 535                 540

Ser Asp Ala Glu Asp Leu Lys Lys Gly Gly Gly Ser Ser Ser Ser His
545                 550                 555                 560

Ser Arg Gln Gln Ser Pro Val Asn Pro Asp Pro Val Ala Leu Asp Ala
                565                 570                 575

His Arg Glu Phe Leu His Arg Pro Ala Ser Gly Tyr Val Pro Glu Glu
            580                 585                 590

Ile Trp Lys Lys Ala Glu Glu Ala Val Asn Glu Val Lys Arg Gln Ala
        595                 600                 605

Met Thr Glu Leu Gln Lys Ala Val Ser Glu Ala Glu Arg Lys Ala His
    610                 615                 620

Asp Met Ile Thr Thr Glu Arg Ala Lys Met Glu Arg Thr Val Ala Glu
625                 630                 635                 640

Ala Lys Arg Gln Ala Ala Glu Asp Ala Leu Ala Val Ile Asn Gln Gln
                645                 650                 655

Glu Asp Ser Ser Glu Ser Cys Trp Asn Cys Gly Arg Lys Ala Ser Glu
            660                 665                 670

Thr Cys Ser Gly Cys Asn Thr Ala Arg Tyr Cys Gly Ser Phe Cys Gln
        675                 680                 685

His Lys Asp Trp Glu Lys His His Ile Cys Gly Gln Thr Leu Gln
690                 695                 700

Ala Gln Gln Gln Gly Asp Thr Pro Ala Val Ser Ser Ser Val Thr Pro
705                 710                 715                 720

Asn Ser Gly Ala Gly Ser Pro Met Asp Thr Pro Pro Ala Ala Thr Pro
                725                 730                 735

Arg Ser Thr Thr Pro Gly Thr Pro Ser Thr Ile Glu Thr Thr Pro Arg
            740                 745                 750
```

<210> SEQ ID NO 8
<211> LENGTH: 575
<212> TYPE: PRT
<213> ORGANISM: Artificial Sequence
<220> FEATURE:
<223> OTHER INFORMATION: Human AML1-ETO 9a

<400> SEQUENCE: 8

```
Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
                20                  25                  30

Ala Pro Asp Ala Gly Ala Ala Leu Ala Gly Lys Leu Arg Ser Gly Asp
            35                  40                  45

Arg Ser Met Val Glu Val Leu Ala Asp His Pro Gly Glu Leu Val Arg
        50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
            100                 105                 110
```

```
Tyr Ser Ala Glu Leu Arg Asn Ala Thr Ala Ala Met Lys Asn Gln Val
            115                 120                 125

Ala Arg Phe Asn Asp Leu Arg Phe Val Gly Arg Ser Gly Arg Gly Lys
130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
                165                 170                 175

Arg Asn Arg Thr Glu Lys His Ser Thr Met Pro Asp Ser Pro Val Asp
            180                 185                 190

Val Lys Thr Gln Ser Arg Leu Thr Pro Pro Thr Met Pro Pro Pro Pro
            195                 200                 205

Thr Thr Gln Gly Ala Pro Arg Thr Ser Ser Phe Thr Pro Thr Thr Leu
    210                 215                 220

Thr Asn Gly Thr Ser His Ser Pro Thr Ala Leu Asn Gly Ala Pro Ser
225                 230                 235                 240

Pro Pro Asn Gly Phe Ser Asn Gly Pro Ser Ser Ser Ser Ser Ser Ser
                245                 250                 255

Leu Ala Asn Gln Gln Leu Pro Pro Ala Cys Gly Ala Arg Gln Leu Ser
            260                 265                 270

Lys Leu Lys Arg Phe Leu Thr Thr Leu Gln Gln Phe Gly Asn Asp Ile
            275                 280                 285

Ser Pro Glu Ile Gly Glu Arg Val Arg Thr Leu Val Leu Gly Leu Val
            290                 295                 300

Asn Ser Thr Leu Thr Ile Glu Glu Phe His Ser Lys Leu Gln Glu Ala
305                 310                 315                 320

Thr Asn Phe Pro Leu Arg Pro Phe Val Ile Pro Phe Leu Lys Ala Asn
                325                 330                 335

Leu Pro Leu Leu Gln Arg Glu Leu Leu His Cys Ala Arg Leu Ala Lys
            340                 345                 350

Gln Asn Pro Ala Gln Tyr Leu Ala Gln His Glu Gln Leu Leu Leu Asp
            355                 360                 365

Ala Ser Thr Thr Ser Pro Val Asp Ser Ser Glu Leu Leu Leu Asp Val
    370                 375                 380

Asn Glu Asn Gly Lys Arg Arg Thr Pro Asp Arg Thr Lys Glu Asn Gly
385                 390                 395                 400

Phe Asp Arg Glu Pro Leu His Ser Glu His Pro Ser Lys Arg Pro Cys
                405                 410                 415

Thr Ile Ser Pro Gly Gln Arg Tyr Ser Pro Asn Asn Gly Leu Ser Tyr
            420                 425                 430

Gln Pro Asn Gly Leu Pro His Pro Thr Pro Pro Pro Gln His Tyr
            435                 440                 445

Arg Leu Asp Asp Met Ala Ile Ala His His Tyr Arg Asp Ser Tyr Arg
450                 455                 460

His Pro Ser His Arg Asp Leu Arg Asp Arg Asn Arg Pro Met Gly Leu
465                 470                 475                 480

His Gly Thr Arg Gln Glu Glu Met Ile Asp His Arg Leu Thr Asp Arg
                485                 490                 495

Glu Trp Ala Glu Glu Trp Lys His Leu Asp His Leu Leu Asn Cys Ile
            500                 505                 510

Met Asp Met Val Glu Lys Thr Arg Arg Ser Leu Thr Val Leu Arg Arg
            515                 520                 525
```

| | | | | | | | | | | | | |
|---|---|---|---|---|---|---|---|---|---|---|---|---|
| Cys | Gln | Glu | Ala | Asp | Arg | Glu | Glu | Leu | Asn | Tyr | Trp | Ile | Arg | Arg | Tyr |
| | 530 | | | | 535 | | | | | 540 | | |

| Ser | Asp | Ala | Glu | Asp | Leu | Lys | Lys | Gly | Gly | Ser | Ser | Ser | His |
|---|---|---|---|---|---|---|---|---|---|---|---|---|---|
| 545 | | | | 550 | | | | 555 | | | | | 560 |

| Ser | Arg | Gln | Gln | Ser | Pro | Val | Asn | Pro | Asp | Pro | Val | Ala | Leu | Asp |
|---|---|---|---|---|---|---|---|---|---|---|---|---|---|---|
| | | | 565 | | | | 570 | | | | 575 |

<210> SEQ ID NO 9
<211> LENGTH: 4272
<212> TYPE: DNA
<213> ORGANISM: Homo sapiens

<400> SEQUENCE: 9

```
catagagcca gcgggcgcgg gcgggacggg cgccccgcgg ccggacccag ccagggcacc      60
acgctgcccg gccctgcgcc gccaggcact tctttccggg gctcctaggg acgccagaag     120
gaagtcaacc tctgctgctt ctccttggcc tgcgttggac cttccttttt ttgttgtttt     180
tttttgtttt tcccctttct tccttttgaa ttaactggct tcttggctgg atgttttcaa     240
cttctttcct ggctgcgaac ttttccccaa ttgttttcct tttacaacag ggggagaaag     300
tgctctgtgg tccgaggcga gccgtgaagt tgcgtgtgcg tggcagtgtg cgtggcagga     360
tgtgcgtgcg tgtgtaaccc gagccgcccg atctgtttcg atctgcgccg cggagccctc     420
cctcaaggcc cgctccacct gctgcggtta cgcggcgctc gtgggtgttc gtgcctcgga     480
gcagctaacc ggcgggtgct gggcgacggt ggaggagtat cgtctcgctg ctgcccgagt     540
cagggctgag tcacccagct gatgtagaca gtggctgcct tccgaagagt gcgtgtttgc     600
atgtgtgtga ctctgcggct gctcaactcc caacaaacca gaggaccagc cacaaactta     660
accaacatcc ccaaacccga gttcacagat gtgggagagc tgtagaaccc tgagtgtcat     720
cgactgggcc ttcttatgat tgttgtttta agattagctg aagatctctg aaacgctgaa     780
ttttctgcac tgagcgtttt gacagaattc attgagagaa cagagaacat gacaagtact     840
tctagctcag cactgctcca actactgaag ctgattttca aggctactta aaaaaatctg     900
cagcgtacat taatggattt ctgttgtgtt taaattctcc acagattgta ttgtaaatat     960
tttatgaagt agagcatatg tatatattta tatatacgtg cacatacatt agtagcacta    1020
cctttggaag tctcagctct tgcttttcgg gactgaagcc agttttgcat gataaaagtg    1080
gccttgttac gggagataat tgtgttctgt tgggacttta gacaaaactc acctgcaaaa    1140
aactgacagg cattaactac tggaacttcc aaataatgtg tttgctgatc gttttactct    1200
tcgcataaat attttaggaa gtgtatgaga attttgcctt caggaacttt tctaacagcc    1260
aaagacagaa cttaacctct gcaagcaaga ttcgtggaag atagtctcca ctttttaatg    1320
cactaagcaa tcggttgcta ggagcccatc ctgggtcaga ggccgatccg cagaaccaga    1380
acgttttccc ctcctggact gttagtaact tagtctccct cctcccctaa ccaccccgc     1440
ccccccccac ccccgcagt aataaaggcc cctgaacgtg tatgttggtc tcccgggagc     1500
tgcttgctga agatccgcgc ccctgtcgcc gtctggtagg agctgtttgc agggtcctaa    1560
ctcaatcggc ttgttgtgat gcgtatcccc gtagatgcca gcacgagccg ccgcttcacg    1620
ccgccttcca ccgcgctgag cccaggcaag atgagcgagg cgttgccgct gggcgccccg    1680
gacgccggcg ctgccctggc cggcaagctg aggagcggcg accgcagcat ggtggaggtg    1740
ctggccgacc acccgggcga gctggtgcgc accgacagcc caacttcct ctgctccgtg     1800
ctgcctacgc actggcgctg caacaagacc ctgcccatcg ctttcaaggt ggtggcccta    1860
```

```
gggatgttc cagatggcac tctggtcact gtgatggctg gcaatgatga aaactactcg    1920
gctgagctga gaaatgctac cgcagccatg aagaaccagg ttgcaagatt taatgacctc    1980
aggtttgtcg gtcgaagtgg aagagggaaa agcttcactc tgaccatcac tgtcttcaca    2040
aacccaccgc aagtcgccac ctaccacaga gccatcaaaa tcacagtgga tgggccccga    2100
gaacctcgaa atcgtactga gaagcactcc acaatgccag actcacctgt ggatgtgaag    2160
acgcaatcta ggctgactcc tccaacaatg ccacctcccc caactactca aggagctcca    2220
agaaccagtt catttacacc gacaacgtta actaatggca cgagccattc tcctacagcc    2280
ttgaatggcg cccctcacc acccaatggc ttcagcaatg ggccttcctc ttcttcctcc    2340
tcctctctgg ctaatcaaca gctgcccca gcctgtggtg ccaggcaact cagcaagctg    2400
aaaaggttcc ttactaccct gcagcagttt ggcaatgaca tttcacccga gataggagaa    2460
agagttcgca ccctcgttct gggactagtg aactccactt tgacaattga agaatttcat    2520
tccaaactgc aagaagctac taacttccca ctgagacctt ttgtcatccc attttttgaag    2580 gccaacttgc ccctgctgca gcgtgagctc ctccactgcg caagactggc caaacagaac    2640
cctgcccagt acctcgccca gcatgaacag ctgcttctgg atgccagcac cacctcacct    2700
gttgactcct cagagctgct tctcgatgtg aacgaaaacg ggaagaggcg aactccagac    2760
agaaccaaag aaaatggctt tgacagagag cctttgcact cagaacatcc aagcaagcga    2820
ccatgcacta ttagcccagg ccagcggtac agtccaaata cggcttatc ctaccagccc    2880 aatggcctgc ctcaccctac cccacctcca cctcagcatt accgtttgga tgatatggcc    2940
attgcccacc actacaggga ctcctatcga caccccagcc acaggacct cagggacaga    3000 aacagaccta tggggttgca tggcacacgt caagaagaaa tgattgatca cagactaaca    3060
gacagagaat gggcagaaga gtggaaacat cttgaccatc tgttaaactg cataatggac    3120
atggtagaaa aaacaaggcg atctctcacc gtactaaggc ggtgtcaaga agcagaccgg    3180
gaagaattga attactggat ccggcggtac agtgacgccg aggacttaaa aaaaggtggc    3240
ggcagtagca gcagccactc taggcagcag agtcccgtca acccagaccc agttgcacta    3300
gacgcgcatc gggaattcct tcacaggcct gcgtctggat acgtgccaga ggagatctgg    3360
aagaaagctg aggaggccgt caatgaggtg aagcgccagg cgatgacgga gctgcagaag    3420
gccgtgtctg aggcggagcg gaaagcccac gacatgatca aacagagag ggccaagatg    3480 gagcgcacgg tcgccgaggc caaacggcag gcggcggagg acgcactggc agttatcaat    3540
cagcaggagg attcaagcga gagttgctgg aattgtggcc gtaaagcgag tgaaacctgc    3600
agtggctgta acacagcccg atactgtggc tcattttgcc agcacaaaga ctgggagaag    3660
caccatcaca tctgtggaca gaccctgcag gcccagcagc agggagacac acctgcagtc    3720
agctcctctg tcacgcccaa cagcggggct gggagcccga tggacacacc accagcagcc    3780
actccgaggt caaccacccc gggaaccct tccaccatag agacaacccc tcgctagacg    3840
tgaactcaga actgtcggag gaaagacaac acaaccaacg cgaaaccaat tcctcatcct    3900
cagatgctca aagttgtttt ttttgtttgt ttgtttatta gatgaattat cctatttcag    3960
tacttcagca agagagaacc taactgtatc ttgaggtggt agtaaaacac agagggccag    4020
taacgggtcg taatgactta ttgtggataa caaagatatc ttttctttag agaactgaaa    4080
agagagcaga gaatataaca tgaaatgata gatttgacct cctccctgtt attttcaagt    4140
agctgggatt ttaaactaga tgacctcatt aaccgatgct ttaccaaaca gcaaaccaag    4200
agattgctaa ttgctgttga aagcaaaaat gctaatatta aaagtcacaa tgttctttat    4260
```

```
atacaataat gg                                                              4272

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: ACT_SITE
<222> LOCATION: (7)..(7)
<223> OTHER INFORMATION: This site may or may not be acetylated.

<400> SEQUENCE: 10

Thr Ala Leu Ser Pro Gly Lys Met Ser Glu Ala
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: ACT_SITE
<222> LOCATION: (4)..(4)
<223> OTHER INFORMATION: This site may or may not be acetylated.

<400> SEQUENCE: 11

Leu Ala Gly Lys Leu Arg Ser Gly Asp Arg Ser
1               5                   10

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide probe

<400> SEQUENCE: 12
gagtggtgtg gtagtgcggt cgggg                                                  25

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide probe

<400> SEQUENCE: 13
gagtggtgtg gtagtgctag cgggg                                                  25
```

METHOD OF TREATING AND REDUCING THE RISK OF ACUTE MYELOGENOUS LEUKEMIA

RELATED APPLICATIONS

This application claims priority to U.S. Provisional Patent Application Ser. No. 61/572,321, filed Jul. 14, 2011; the entirety of which is hereby incorporated by reference.

GOVERNMENT SUPPORT

The United States Government has provided grant support utilized in the development of the present invention. In particular, National Institutes of Health grant number GM62437 has supported development of this invention. The United States Government may have certain rights in the invention.

BACKGROUND

Leukemia is a disease in which immature hematopoietic stem cells are developed and proliferate abnormally in bone marrow. Leukemia is classified into 4 types (acute myeloid leukemia, chronic myeloid leukemia, acute lymphocytic leukemia and chronic lymphocytic leukemia) depending on type of developed cells and proliferation rate thereof. Myelodysplastic syndrome is also included in leukemia because of its similarity and correlation in findings.

Acute leukemia is a disease in which hematopoietic stem cells and/or progenitor cells are developed and only specific cells proliferate as leukemia cells. On the other hand, chronic leukemia is a disease in which stem cells per se proliferate autonomously but maintain ability to differentiate into mature cells, and only cells originated from a certain clone proliferate autonomously. Myelodysplastic syndrome is a disease in which hematopoietic stem cells acquire genetic abnormality a posteriori and thereby presenting cytopenia and/or dysplasia in hematopoietic system.

SUMMARY

The present invention encompasses the recognition that reproducible and detectable changes in AML1-ETO acetylation are associated with incidence and/or risk of Acute Myelogenous Leukemia (AML), specifically in individuals with t(8;21)(q22;q22) translocations. The present invention permits identification and/or characterization of novel agents to treat and/or reduce risk of AML by virtue of their effect on AML1-ETO acetylation. The present invention also provides systems for using such agents, for example to treat and/or reduce risk of AML.

In certain embodiments, the present disclosure provides methods of identifying agents for treating or reducing risk for acute myelogenous leukemia comprising providing a system in which AML1-ETO acetylation level is determinable, contacting the system with a test agent, determining AML1-ETO acetylation level when the test agent is present, comparing the determined AML1-ETO acetylation level with a reference AML1-ETO acetylation level so that any difference between the reference level and the determined level is detected, and characterizing the test agent's usefulness in treating or reducing risk for acute myelogenous leukemia based on the detected difference. In some embodiments, the reference AML1-ETO acetylation level is that observed in the system or a comparable system under comparable conditions lacking the test agent. In some embodiments, the reference AML1-ETO acetylation level is that observed in the system or a comparable system under otherwise identical conditions lacking the test agent. In some embodiments, the reference AML1-ETO acetylation level is that observed in the system or a comparable system under comparable conditions that include presence of a positive control agent. In some embodiments, the reference AML1-ETO acetylation level is that observed in the system or a comparable system under comparable conditions that include presence of a negative control agent. In some embodiments, the reference AML1-ETO acetylation level is a historical level. In some embodiments, the system is an in vitro system. In some embodiments, the in vitro system comprises cultured cells. In some embodiments, the acetylation level of AML1-ETO comprises acetylation on amino acid K43.

In certain embodiments, the present disclosure provides methods of treating or reducing risk for acute myelogenous leukemia comprising administering to a subject one or more AML1-ETO acetylation inhibitors.

In certain embodiments, the present disclosure provides methods of identifying agents for treating or reducing risk for acute myelogenous leukemia comprising determining transcription levels of one or more targets of AML1-ETO transcriptional activation contacted to a test agent and identifying the test agent as treating or reducing risk for acute myelogenous leukemia if the transcription levels are reduced relative to transcription levels in comparable conditions lacking the test agent. In some embodiments, the one or more targets of AML1-ETO transcriptional activation comprise Id1, p21 or Egr1.

In certain embodiments, the present disclosure provides methods of treating or reducing risk for acute myelogenous leukemia comprising administering to a subject one or more agents characterized in that transcription levels of one or more targets of AML1-ETO transcriptional activation are lower in the agent's presence as compared with in its absence.

DEFINITIONS

Figure 1:
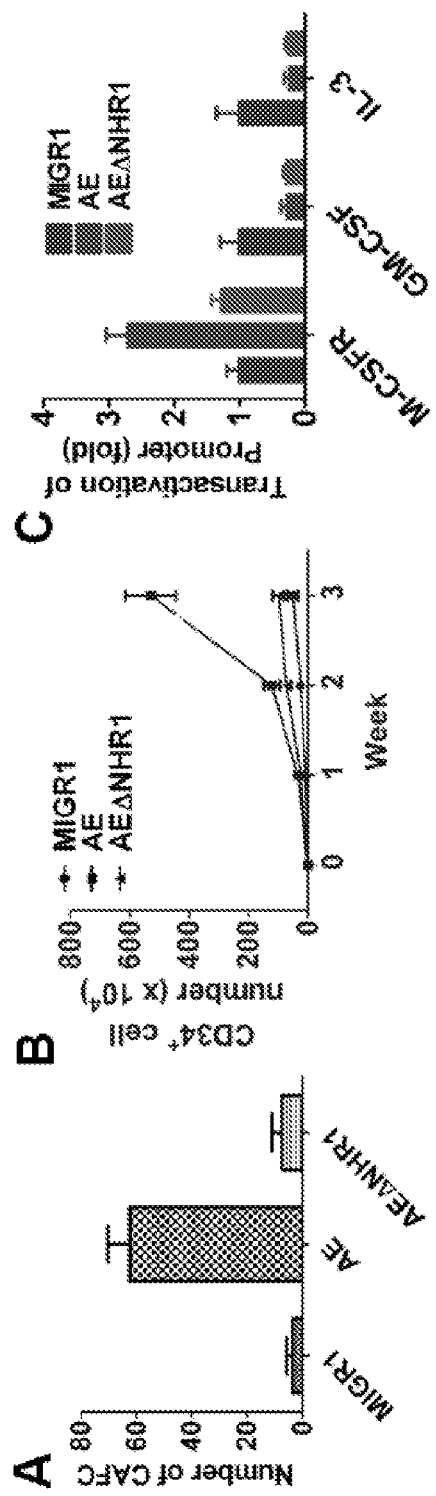
FIGS. 1A-1C shows enhanced self-renewal capacity and transcriptional activation induced by A-E in human hematopoietic stem/progenitor cells requires the NHR1 domain. (A) The NHR1 domain (aa245-436) is required for A-E to increase CAFC formation by human CD34$^+$ cells transduced with the indicated retroviral vector. The number of cobblestone areas at week 5 is shown ±SD (n=3). (B) Deletion of NHR1 affects the ability of A-E to promote self-renewal in liquid culture. CD34$^+$ expression was examined weekly in MIGR1, AE and AEΔNHR1 transduced human CD34$^+$ cells (±SD; n=3). (C) M-CSFR, GM-CSF and IL-3 promoter activity was examined in cells transduced with MIGR1, AE or AEΔNHR1 (±SD; n=3). All values were standardized to the level of *Renilla* luciferase activity.

Acetyl: As used herein, the term "acetyl" (also known as "ethanoyl" and often abbreviated as "Ac") is used herein to refer to a functional group with the chemical formula —COCH$_3$.

Acetylated: As used herein, the term "acetylated" means modified by covalent addition of an acetyl group. For example, an acetylated glycan is a glycan that is modified by covalent addition of one or more acetyl groups. An acetylated glycan may or may not have additional modifications.

Acetylation: As used herein, the term "acetylation" (also known in IUPAC nomenclature as "ethanoylation") refers to the process of covalently adding one or more acetyl groups to a molecule (e.g., to a glycan).

Agents: As used herein, the term "agents" (also referred to as "test agents") refers to any compounds or compositions that can be tested as potential modulators (e.g., inhibitors or activators). Examples of agents that can be used include, but are not limited to, small molecules, antibodies, antibody fragments, siRNAs, shRNAs, nucleic acid molecules (RNAs, DNAs, or DNA/RNA hybrids), antisense oligonucleotides, ribozymes, peptides, peptide mimetics, carbohydrates, lipids, microorganisms, natural products, and the like. In some embodiments, an agent can be isolated or not isolated. As a non-limiting example, test agents can be a library of agents. If a mixture of agents is found to be a modulator (e.g., an inhibitor), the pool can then be further purified into separate components to determine which component is in fact the modulator (e.g., inhibitor) of a target activity.

Carrier or diluent: As used herein, the terms "carrier" and "diluent" refers to a pharmaceutically acceptable (e.g., safe and non-toxic for administration to a human) carrier or diluting substance useful for preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

Comparable: The term "comparable" as used herein refers to a system, set of conditions, effects, or results that is/are sufficiently similar to a test system, set of conditions, effects, or results, to permit scientifically legitimate comparison. Those of ordinary skill in the art will appreciate and understand which systems, sets of conditions, effect, or results are sufficiently similar to be "comparable" to any particular test system, set of conditions, effects, or results as described herein.

Dosage form: As used herein, the terms "dosage form" and "unit dosage form" refer to a physically discrete unit of a therapeutic agent for a patient to be treated. Each unit contains a predetermined quantity of active material calculated to produce a desired therapeutic effect. It will be understood, however, that a total dosage of the composition will be decided by an attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, the therapeutic agent is administered continuously over a predetermined period. In some embodiments, the therapeutic agent is administered once a day (QD) or twice a day (BID).

Improve, increase, or reduce: As used herein, the terms "improve," "increase" or "reduce," or grammatical equivalents, indicate values that are relative to a comparable baseline or reference measurement. In some embodiments, a comparable baseline or reference measurement is a measurement in the same individual prior to initiation of treatment described herein, or a measurement in a control individual (or multiple control individuals) in the absence of treatment described herein. In some embodiments "control individual" is an individual afflicted with the same form of disease as an individual being treated, who is about the same age as an individual being treated (to ensure that stages of disease in the treated individual and the control individual(s) are comparable).

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Nucleic Acid: The terms "nucleic acid", "nucleic acid molecule", and "polynucleotide" each is used herein to refer to a polymers of nucleotide monomers or analogs thereof, such as deoxyribonucleic acid (DNA) and ribonucleic acid (RNA). Unless otherwise stated, the terms encompass nucleic acid-like structures with synthetic backbones, as well as amplification products. In some embodiments, nucleic acids involved in the present invention are linear nucleic acids.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having the complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder or condition (AML) comprises a likelihood that a particular individual will develop a disease, disorder, or condition. In some embodiments, risk is expressed as a percentage. In some embodiments, risk is from 0, 1, 2, 3, 4, 5, 6, 7, 8, 9, 10 up to 100%. In some embodiments risk is expressed as a risk relative to a risk associated with a reference sample or group of reference samples. In some embodiments, a reference sample or group of reference samples have a known risk of a disease, disorder, or condition (AML). In some embodiments a reference sample or group of reference samples are from individuals comparable to a particular individual. In some embodiments, relative risk is 0, 1, 2, 3, 4, 5, 6, 7, 8, 9, 10 or more.

Reference: As will be understood from context, a reference sample, population, or individual is one that is sufficiently similar to a particular sample, population, or individual of interest to permit a relevant comparison (i.e., to be comparable). In some embodiments, information about a reference sample is obtained simultaneously with information about a particular sample. In some embodiments, information about a reference sample is historical. In some embodiments, information about a reference sample is stored for example in a computer-readable medium. In some embodiments, comparison of a particular sample of interest with a reference sample establishes identity with, similarity to, or difference of a particular sample of interest relative to a reference.

Sample: As used herein, the term "sample" typically refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Suffering from: An individual who is "suffering from" a disease, disorder, and/or condition has been diagnosed with or displays one or more symptoms of the disease, disorder, and/or condition.

Therapeutically effective amount: As used herein, the term "therapeutically effective amount" refers to an amount of an agent which confers a therapeutic effect on a treated subject, at a reasonable benefit/risk ratio applicable to any medical treatment. A therapeutic effect may be objective (i.e., measurable by some test or marker) or subjective (i.e., subject gives an indication of or feels an effect). In particular, a "therapeutically effective amount" refers to an amount of a therapeutic agent effective to treat, ameliorate, or prevent a desired disease or condition, or to exhibit a detectable therapeutic or preventative effect, such as by ameliorating symptoms associated with a disease, preventing or delaying onset of a disease, and/or also lessening severity or frequency of symptoms of a disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, on combination with other agents. Also, a specific therapeutically effective amount (and/or unit dose) for any particular patient may depend upon a variety of factors including what disorder is being treated; disorder severity; activity of specific agents employed; specific composition employed; age, body weight, general health, sex and diet of a patient; time of administration, route of administration; treatment duration; and like factors as is well known in the medical arts.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Vector: As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

DETAILED DESCRIPTION OF CERTAIN EMBODIMENTS

Leukemia

Leukemia is a malignant cancer of bone marrow and blood. It is characterized by uncontrolled growth of blood cells. Common types of leukemia are divided into four categories: acute or chronic myelogenous, involving myeloid elements of the bone marrow (white cells, red cells, megakaryocytes) and acute or chronic lymphocytic, involving cells of the lymphoid lineage.

Acute leukemia is a rapidly progressing disease that results in massive accumulation of immature, functionless cells (blasts) in the marrow and blood. The marrow often can no longer produce enough normal red and white blood cells and platelets. Anemia, a deficiency of red cells, develops in virtually all leukemia patients. Lack of normal white cells impairs the body's ability to fight infections. A shortage of platelets results in bruising and easy bleeding. In contrast, chronic leukemia progresses more slowly and leads to unregulated proliferation and hence marked overexpansion of a spectrum of mature (differentiated) cells. In general, acute leukemia, unlike chronic leukemia, is potentially curable by elimination of the neoplastic clone.

Treatment of leukemia is very complex and depends upon leukemia type. Tremendous clinical variability among remissions is also observed in leukemic patients, even those that occur after one course of therapy. Patients who are resistant to therapy have very short survival times, regardless of when resistance occurs.

Standard treatment for leukemia usually involves chemotherapy and/or bone marrow transplantation and/or radiation therapy. Two major types of bone marrow transplants are autologus (uses a patient's own marrow) and allogeneic (uses marrow from a compatible donor). Radiation therapy, which involves use of high-energy rays, and chemotherapy are usually given before bone marrow transplantation to kill all leukemic cells. Bone marrow transplantation can be clearly curative of CML. However, only 30% to 40% of patients with CML have an appropriate donor. Additionally, mortality from the procedure ranges from 20% to 30%, depending on the age of the recipient.

Chemotherapy in leukemia may involve a combination of two or more anti-cancer drugs. Approximately 40 different drugs are now being used in the treatment of leukemia, either alone or in combination. Some common combinations include cytarabine with either doxorubicin or daunorubicin or mitoxantrone or thioguanine, mercaptopurine with methotrexate, mitroxantrone with etoposide, asparaginase with vincristine, daunorubicin and prednisone, cyclophosphamide with vincristine, cytarabine and prednisone, cyclophosphamide with vincristine and prednisone, daunorubicin with cytarabine and thioguanine and daunorubicin with vincristine and prednisone.

Acute Myelogenous Leukemia

Acute Myelogenous Leukemia (AML) is an aggressive form of leukemia that generally warrants urgent and intensive therapy. The average patient age at AML diagnosis is 64-68 years old, and patients over the age of 60 treated with standard chemotherapy are cured of their disease <20% of the time. Patients who develop AML after an antecedent hematologic disorder or prior leukemogenic chemotherapy/radiation therapy have similarly poor outcomes, as do patients whose disease is associated with specific adverse cytogenetic and clinical features. Hence, most patients diagnosed with AML have patient and/or disease-related features that are associated with a very poor prognosis. For patients with relapsed disease, no standard non-transplant therapy has demonstrated a capacity as a cure. For these patients, AML is often a fatal disease. New approaches to therapy of AML are needed.

Current AML therapy regimens generally involve two stages: Initial treatment ("induction therapy") for AML is aimed at eradicating leukemic clones to re-establish normal hematopoiesis, and post-remission therapy. AML treatment generally involves chemotherapy, and sometimes involves radiation therapy to relieve AML-induced bone pain. For patients who have relapses or have AML that does not respond to other treatment, bone marrow transplantation ("BMT") may be required, and can often increase survival.

Certain chromosomal abnormalities are routinely used to determine prognosis in adult AML patients, including t(8;21), t(15;17) or inv(16) suggestive of better prognosis; t(9;11) used to classify patients at intermediate risk; and inv(3), −5/del(5q), −7/del(7q), t(6;9), abnormalities involving 11q23, or a complex karyotype (three or more cytogenetic aberrations) used to classify patient as being at high risk (Valk et al., New England J of Medicine, 350(16):1617-1628; Bullinger et al., New England J. of Medicine, 350 (16):1605-1616 (2004)). A significant proportion of AML patients do not exhibit such genetic abnormalities. However, physiological effects of these chromosomal anomalies represent potential therapeutic targets for a subset of AML patients.

AML1-ETO

The present invention encompasses the recognition that the AML1-ETO has useful diagnostic and therapeutic purposes relating to AML.

AML1 is a transcription factor with significant homology to the *Drosophila* segmentation gene, Runt (Miyoshi et al., 1991; Erickson et al., 1992). It binds the enhancer core target sequence, TGT/cGGT, in association with a non-DNA-binding subunit, CBFβ (Wang et al., 1993; Ogawa et al., 1993; Meyers et al., 1993; Bravo et al., 2001). Both proteins (together referred to as core binding factor or CBF) interact through the DNA-binding Runt homology domain of AML1. Null mutations in either CBF subunit in mice resulted in embryonic lethality that was associated with intra-cranial hemorrhaging and a complete absence of definitive hematopoiesis (Okuda et al., 1996; Wang et al., 1996a; Wang et al., 1996b; Sasaki et al., 1996). A complete absence of hematopoietic cells in AML1 knockout animals indicates that AML1 is essential for formation of differentiated blood cells from HSCs (Okuda et al., 1996).

Mutations in the AML1 gene, including chromosomal translocations, represent one of the most common genetic abnormalities observed in leukemia. The t(8;21)(q22;q22) translocation, which fuses the ETO gene on human chromosome 8 with the AML1 gene on chromosome 21, is seen in approximately 12-15% of acute myelogenous leukemia (AML) cases, and in about 40% of AML with a French-American-British classified M2 phenotype (reviewed in Nucifera and Rowley, 1995; Downing, 1999). The t(8;21) translocation fuses the N-terminal 177 amino acids of AML1, which includes the Runt homology domain that binds DNA and interacts with CBFβ, in frame with amino acids 30-604 of ETO. The fusion protein deletes the C-terminal activation domain of AML1. The ETO gene is homologous to the *Drosophila* gene, nervy, and can associate with transcriptional co-repressor complexes that include mSin3, histone deacetylates (HDACs), and nuclear hormone co-repressors, which are involved in transcriptional repression (Lutterbach et al., 1998). Gene knock-in experiments in mice have shown that AML1-ETO acts in a dominant-repressive manner to block AML1-dependent transcription (Yergeau et al., 1997; Okuda et al., 1998). Animals heterozygous for an AML1-ETO knock-in allele displayed a similar phenotype to AML1 or CBFβ knock-out mice in that they died early in embryonic life (e13.5) and exhibited intra-cranial bleeding and a block in definitive hematopoiesis. One important difference between knock-out and knock-in phenotypes was the presence of dysplastic hematopoietic progenitor cells within fetal livers of knock-in mice that could readily be established as immortalized cell lines in vitro (Okuda et al., 1998). The similarity of AML1 knockout results with AML1-ETO knock-in mice indicates that AML1 is an important target protein for HSC function and may be a primary effector protein for HSC self-renewal, since there are no definitive hematopoietic cells in the absence of AML1. These results may also indicate that AML1 is important for HSC differentiation into various blood cell lineages.

AML1-ETO has been purified, characterized, cloned and sequenced from both mouse and human sources. AML1-ETO protein contains 752 amino acid residues, the amino acid sequence of which is shown in Table 1. It is primarily expressed in hematopoietic cells of non-lymphoid lineages.

TABLE 1

| Human AML1-ETO Protein Sequence (GeneBank: BAA03089.1) | MRIPVDASTSRRFTPPSTALSPGKMSEALPLGA PDAGAALAGKLRSGDRSMVEVLADHPGELVRTD SPNFLCSVLPTHWRCNKTLPIAFKVVALGDVPD GTLVTVMAGNDENYSAELRNATAAMKNQVARFN DLRFVGRSGRGKSFTLTITVFTNPPQVATYHRA IKITVDGPREPRNRTEKHSTMPDSPVDVKTQSR LTPPTMPPPPTTQGAPRTSSFTPTTLTNGTSHS PTALNGAPSPPNGFSNGPSSSSSSSLANQQLPP ACGARQLSKLKRFLTTLQQFGNDISPEIGERVR TLVLGLVNSTLTIEEFHSKLQEATNFPLRPFVI PFLKANLPLLQRELLHCARLAKQNPAQYLAQHE QLLLDASTTSPVDSSELLLDVNENGKRRTPDRT KENGFDREPLHSEHPSKRPCTISPGQRYSPNNG LSYQPNGLPHPTPPPPQHYRLDDMAIAHHYRDS YRHPSHRDLRDRNRPMGLHGTRQEEMIDHRLTD REWAEEWKHLDHLLNCIMDMVEKTRRSLTVLRR CQEADREELNYWIRRYSDAEDLKKGGGSSSSHS RQQSPVNPDPVALDAHREFLHRPASGYVPEEIW KKAEEEAVNEVKRQAMTELQKAVSEAERKAHDMI TTERAKMERTVAEAKRQAAEDALAVINQQEDSS ESCWNCGRKASETCSGCNTARYCGSFCQHKDWE |
|---|---|

TABLE 1-continued

| | |
|---|---|
| Human AML1-ETO ΔNHR1 Protein Sequence | KHHHICGQTLQAQQQGDTPAVSSSVTPNSGAGS PMDTPPAATPRSTTPGTPSTIETTPR (SEQ ID NO: 1)<br><br>MRIPVDASTSRRFTPPSTALSPGKMSEALPLGA PDAGAALAGKLRSGDRSMVEVLADHPGELVRTD SPNFLCSVLPTHWRCNKTLPIAFKVVALGDVPD GTLVTVMAGNDENYSAELRNATAAMKNQVARFN DLRFVGRSGRGKSFTLTITVFTNPPQVATYHRA IKITVDGPREPRNRTEKHSTMPDSPVDVKTQSR LTPPTMPPPPTTQGAPRTSSFTPTTLTNGTSHS PTALNGAPSPPNGFSHRDLRDRNRPMGLHGTRQ EEMIDHRLTDREWAEEWKHLDHLLNCIMDMVEK TRRSLTVLRRCQEADREELNYWIRRYSDAEDLK KGGGSSSSHSRQQSPVNPDPVALDAHREFLHRP ASGYVPEEIWKKAEEAVNEVKRQAMTELQKAVS EAERKAHDMITTERAKMERTVAEAKRQAAEDAL AVINQQEDSSESCWNCGRKASETCSGCNTARYC GSFCQHKDWEKHHHICGQTLQAQQQGDTPAVSS SVTPNSGAGSPMDTPPAATPRSTTPGTPSTIET TPR (SEQ ID NO: 2) |
| Human AML1-ETO ΔNHR2 Protein Sequence | MRIPVDASTSRRFTPPSTALSPGKMSEALPLGA PDAGAALAGKLRSGDRSMVEVLADHPGELVRTD SPNFLCSVLPTHWRCNKTLPIAFKVVALGDVPD GTLVTVMAGNDENYSAELRNATAAMKNQVARFN DLRFVGRSGRGKSFTLTITVFTNPPQVATYHRA IKITVDGPREPRNRTEKHSTMPDSPVDVKTQSR LTPPTMPPPPTTQGAPRTSSFTPTTLTNGTSHS PTALNGAPSPPNGFSNGPSSSSSSSLANQQLPP ACGARQLSKLKRFLTTLQQFGNDISPEIGERVR TLVLGLVNSTLTIEEFHSKLQEATNFPLRPFVI PFLKANLPLLQRELLHCARLAKQNPAQYLAQHE QLLLDASTTSPVDSSELLLDVNENGKRRTPDRT KENGFDREPLHSEHPSKRPCTISPGQRYSPNNG LSYQPNGLPHPTPPPPQHYRLDDMAIAHHYRDS YRHPSHRDLRDRNRPMGLEDLKKGGGSSSSHSR QQSPVNPDPVALDAHREFLHRPASGYVPEEIVV KKAEEAVNEVKRQAMTELQKAVSEAERKAHDMI TTERAKMERTVAEAKRQAAEDALAVINQQEDSS ESCWNCGRKASETCSGCNTARYCGSFCQHKDWE KHHHICGQTLQAQQQGDTPAVSSSVTPNSGAGS PMDTPPAATPRSTTPGTPSTIETTPR (SEQ ID NO: 3) |
| Human AML1-ETO ΔRunt Protein Sequence | MRIPVDASTSRRFTPPSTALSPGKMSEALPLGA PDAGAALAGKLRSGDKHSTMPDSPVDVKTQSRL TPPTMPPPPTTQGAPRTSSFTPTTLTNGTSHSP TALNGAPSPPNGFSNGPSSSSSSSLANQQLPPA CGARQLSKLKRFLTTLQQFGNDISPEIGERVRT LVLGLVNSTLTIEEFHSKLQEATNFPLRPFVIP FLKANLPLLQRELLHCARLAKQNPAQYLAQHEQ LLLDASTTSPVDSSELLLDVNENGKRRTPDRTK ENGFDREPLHSEHPSKRPCTISPGQRYSPNNGL SYQPNGLPHPTPPPPQHYRLDDMAIAHHYRDSY RHPSHRDLRDRNRPMGLHGTRQEEMIDHRLTDR EWAEEWKHLDHLLNCIMDMVEKTRRSLTVLRRC QEADREELNYWIRRYSDAEDLKKGGGSSSSHSR QQSPVNPDPVALDAHREFLHRPASGYVPEEIVV KKAEEAVNEVKRQAMTELQKAVSEAERKAHDMI TTERAKMERTVAEAKRQAAEDALAVINQQEDSS ESCWNCGRKASETCSGCNTARYCGSFCQHKDWE KHHHICGQTLQAQQQGDTPAVSSSVTPNSGAGS PMDTPPAATPRSTTPGTPSTIETTPR (SEQ ID NO: 4) |
| Human AML1-ETO K24R Protein Sequence | MRIPVDASTSRRFTPPSTALSPGRMSEALPLGA PDAGAALAGKLRSGDRSMVEVLADHPGELVRTD SPNFLCSVLPTHWRCNKTLPIAFKVVALGDVPD GTLVTVMAGNDENYSAELRNATAAMKNQVARFN DLRFVGRSGRGKSFTLTITVFTNPPQVATYHRA IKITVDGPREPRNRTEKHSTMPDSPVDVKTQSR LTPPTMPPPPTTQGAPRTSSFTPTTLTNGTSHS PTALNGAPSPPNGFSNGPSSSSSSSLANQQLPP ACGARQLSKLKRFLTTLQQFGNDISPEIGERVR TLVLGLVNSTLTIEEFHSKLQEATNFPLRPFVI PFLKANLPLLQRELLHCARLAKQNPAQYLAQHE QLLLDASTTSPVDSSELLLDVNENGKRRTPDRT KENGFDREPLHSEHPSKRPCTISPGQRYSPNNG LSYQPNGLPHPTPPPPQHYRLDDMAIAHHYRDS YRHPSHRDLRDRNRPMGLHGTRQEEMIDHRLTD REWAEEWKHLDHLLNCIMDMVEKTRRSLTVLRR CQEADREELNYWIRRYSDAEDLKKGGGSSSSHS RQQSPVNPDPVALDAHREFLHRPASGYVPEEIW KKAEEAVNEVKRQAMTELQKAVSEAERKAHDMI TTERAKMERTVAEAKRQAAEDALAVINQQEDSS ESCWNCGRKASETCSGCNTARYCGSFCQHKDWE KHHHICGQTLQAQQQGDTPAVSSSVTPNSGAGS PMDTPPAATPRSTTPGTPSTIETTPR (SEQ ID NO: 5) |
| Human AML1-ETO K43R Protein Sequence | MRIPVDASTSRRFTPPSTALSPGKMSEALPLGA PDAGAALAGRLRSGDRSMVEVLADHPGELVRTD SPNFLCSVLPTHWRCNKTLPIAFKVVALGDVPD GTLVTVMAGNDENYSAELRNATAAMKNQVARFN DLRFVGRSGRGKSFTLTITVFTNPPQVATYHRA IKITVDGPREPRNRTEKHSTMPDSPVDVKTQSR LTPPTMPPPPTTQGAPRTSSFTPTTLTNGTSHS PTALNGAPSPPNGFSNGPSSSSSSSLANQQLPP ACGARQLSKLKRFLTTLQQFGNDISPEIGERVR TLVLGLVNSTLTIEEFHSKLQEATNFPLRPFVI PFLKANLPLLQRELLHCARLAKQNPAQYLAQHE QLLLDASTTSPVDSSELLLDVNENGKRRTPDRT KENGFDREPLHSEHPSKRPCTISPGQRYSPNNG LSYQPNGLPHPTPPPPQHYRLDDMAIAHHYRDS YRHPSHRDLRDRNRPMGLHGTRQEEMIDHRLTD REWAEEWKHLDHLLNCIMDMVEKTRRSLTVLRR CQEADREELNYWIRRYSDAEDLKKGGGSSSSHS RQQSPVNPDPVALDAHREFLHRPASGYVPEEIW KKAEEAVNEVKRQAMTELQKAVSEAERKAHDMI TTERAKMERTVAEAKRQAAEDALAVINQQEDSS ESCWNCGRKASETCSGCNTARYCGSFCQHKDWE KHHHICGQTLQAQQQGDTPAVSSSVTPNSGAGS PMDTPPAATPRSTTPGTPSTIETTPR (SEQ ID NO: 6) |
| Human AML1-ETO K24R K43R Protein Sequence | MRIPVDASTSRRFTPPSTALSPGRMSEALPLGA PDAGAALAGRLRSGDRSMVEVLADHPGELVRTD SPNFLCSVLPTHWRCNKTLPIAFKVVALGDVPD GTLVTVMAGNDENYSAELRNATAAMKNQVARFN DLRFVGRSGRGKSFTLTITVFTNPPQVATYHRA IKITVDGPREPRNRTEKHSTMPDSPVDVKTQSR LTPPTMPPPPTTQGAPRTSSFTPTTLTNGTSHS PTALNGAPSPPNGFSNGPSSSSSSSLANQQLPP ACGARQLSKLKRFLTTLQQFGNDISPEIGERVR TLVLGLVNSTLTIEEFHSKLQEATNFPLRPFVI PFLKANLPLLQRELLHCARLAKQNPAQYLAQHE QLLLDASTTSPVDSSELLLDVNENGKRRTPDRT KENGFDREPLHSEHPSKRPCTISPGQRYSPNNG LSYQPNGLPHPTPPPPQHYRLDDMAIAHHYRDS YRHPSHRDLRDRNRPMGLHGTRQEEMIDHRLTD REWAEEWKHLDHLLNCIMDMVEKTRRSLTVLRR CQEADREELNYWIRRYSDAEDLKKGGGSSSSHS RQQSPVNPDPVALDAHREFLHRPASGYVPEEIW KKAEEAVNEVKRQAMTELQKAVSEAERKAHDMI TTERAKMERTVAEAKRQAAEDALAVINQQEDSS ESCWNCGRKASETCSGCNTARYCGSFCQHKDWE KHHHICGQTLQAQQQGDTPAVSSSVTPNSGAGS PMDTPPAATPRSTTPGTPSTIETTPR (SEQ ID NO: 7) |
| Human AML1-ETO 9a Protein Sequence | MRIPVDASTSRRFTPPSTALSPGKMSEALPLGA PDAGAALAGKLRSGDRSMVEVLADHPGELVRTD SPNFLCSVLPTHWRCNKTLPIAFKVVALGDVPD GTLVTVMAGNDENYSAELRNATAAMKNQVARFN DLRFVGRSGRGKSFTLTITVFTNPPQVATYHRA IKITVDGPREPRNRTEKHSTMPDSPVDVKTQSR LTPPTMPPPPTTQGAPRTSSFTPTTLTNGTSHS PTALNGAPSPPNGFSNGPSSSSSSSLANQQLPP ACGARQLSKLKRFLTTLQQFGNDISPEIGERVR TLVLGLVNSTLTIEEFHSKLQEATNFPLRPFVI PFLKANLPLLQRELLHCARLAKQNPAQYLAQHE QLLLDASTTSPVDSSELLLDVNENGKRRTPDRT KENGFDREPLHSEHPSKRPCTISPGQRYSPNNG LSYQPNGLPHPTPPPPQHYRLDDMAIAHHYRDS YRHPSHRDLRDRNRPMGLHGTRQEEMIDHRLTD REWAEEWKHLDHLLNCIMDMVEKTRRSLTVLRR CQEADREELNYWIRRYSDAEDLKKGGGSSSSHS RQQSPVNPDPVALD (SEQ ID NO: 8) |

In some embodiments, an AML1-ETO protein is or comprises any protein that shares at least 70% sequence identity with SEQ ID NO:1, or, in some embodiments, with a portion thereof (preferably comprising at least 10, 15, 20, 25, 30, 35, 40, 45, 50, 55, 60, 65, 70, 75, 80, 85, 90, 95, 100 amino acids or more consecutive amino acids of SEQ ID NO:1). In some embodiments, an AML1-ETO protein lacks the NHR1 domain (amino acids 245-436) (SEQ ID NO: 2) that is found in SEQ ID NO:1. In some embodiments, an AML1-ETO protein lacks the NHR2 domain (amino acids 481 to 547) (SEQ ID NO: 3) that is found in SEQ ID NO:1. In some embodiments, an AML1-ETO protein lacks the Runt domain (amino acids 48 to 182) (SEQ ID NO: 4) that is found in SEQ ID NO:1. In some embodiments, an AML1-ETO protein is or comprises AML1-ETO K24R (SEQ ID NO: 5). In some embodiments, an AML1-ETO protein is or comprises AML1-ETO K43R (SEQ ID NO: 6). In some embodiments, an AML1-ETO protein is or comprises AML1-ETO K24R K43R (SEQ ID NO: 7). In some embodiments, an AML1-ETO protein is or comprises AML1-ETO9a (SEQ ID NO: 8).

AML1-ETO Expression

Polynucleotides (e.g., DNA fragments) encoding an AML1-ETO protein can be generated by any of a variety of procedures. They can be cleaved from larger polynucleotides (e.g., genomic sequences, cDNA, or the like) with appropriate restriction enzymes, which can be selected, for example, on the basis of published sequences of human AML1-ETO. The mRNA sequence for human AML1-ETO is shown in Table 2.

TABLE 2

| Human AML1-ETO mRNA Sequence (GeneBank: BAA03089.1) | CATAGAGCCAGCGGGCGCGGGCGGGACGGGCGC CCCGCGGCCGGACCCAGCCAGGGCACCACGCTG CCCGGCCCTGCGCCGCCAGGCACTTCTTTCCGG GGCTCCTAGGGACGCCAGAAGGAAGTCAACCTC TGCGTTGGACCTTCCTTTTTTTGTTGTTTTTTT TTGTTTTTCCCCTTTCTTCCTTTTGAATTAACT GGCTTCTTGGCTGGATGTTTTCAACTTCTTTCC TGGCTGCGAACTTTTCCCCAATTGTTTTCCTTT TACAACAGGGGGAGAAAGTGCTCTGTGGTCCGA GGCGAGCCGTGAAGTTGCGTGTGCGTGGCAGTG TGCGTGGCAGGATGTGCGTGCGTGTGTAACCCG AGCCGCCCGATCTGTTTCGATCTGCGCCGCGGA GCCCTCCCTCAAGGCCCGCTCCACCTGCTGCGG TTACGCGGCGCTCGTGGGTGTTCGTGCCTCGGA GCAGCTAACCGGCGGGTGCTGGGCGACGGTGGA GGAGTATCGTCTCGCTGCTGCCCGAGTCAGGGC TGAGTCACCCAGCTGATGTAGACAGTGGCTGCC TTCCGAAGAGTGCGTGTTTGCATGTGTGTGACT CTGCGGCTGCTCAACTCCCAACAAACCAGAGGA CCAGCCACAAACTTAACCAACATCCCCAAACCC GAGTTCACAGATGTGGGAGAGCTGTAGAACCCT GAGTGTCATCGACTGGGCCTTCTTATGATTGTT GTTTTAAGATTAGCTGAAGATCTCTGAAACGCT GAATTTTCTGCACTGAGCGTTTTGACAGAATTC ATTGAGAACAGAGAACATGACAAGTACTTCT AGCTCAGCACTGCTCCAACTACTGAAGCTGATT TTCAAGGCTACTTAAAAAAATCTGCAGCGTACA TTAATGGATTTCTGTTGTGTTTAAATTCTCCAC AGATTGTATTGTAAATATTTTATGAAGTAGAGC ATATGTATATATTTATATATACGTGCACATACA TTAGTAGCACTACCTTTGGAAGTCTCAGCTCTT GCTTTTCGGGACTGAAGCCAGTTTTGCATGATA AAAGTGGCCTTGTTACGGGAGATAATTGTGTTC TGTTGGGACTTTAGACAAAACTCACCTGCAAAA AACTGACAGGCATTAACTACTGGAACTTCCAAA TAATGTGTTTGCTGATCGTTTTACTCTTCGCAT AAATATTTTAGGAAGTGTATGAGAATTTTGCCT TCAGGAACTTTTCTAACAGCCAAAGACAGAACT TAACCTCTGCAAGCAAGATTCGTGGAAGATAGT CTCCACTTTTTAATGCACTAAGCAATCGGTTGC TAGGAGCCCATCCTGGGTCAGAGGCCGATCCGC |

TABLE 2-continued

AGAACCAGAACGTTTTCCCCTCCTGGACTGTTA
GTAACTTAGTCTCCCTCCTCCCCTAACCACCCC
CGCCCCCCCCCACCCCCCGCAGTAATAAAGGCC
CCTGAACGTGTATGTTGGTCTCCCGGGAGCTGC
TTGCTGAAGATCCGCGCCCCTGTCGCCGTCTGG
TAGGAGCTGTTTGCAGGGTCCTAACTCAATCGG
CTTGTTGTGATGCGTATCCCCGTAGATGCCAGC
ACGAGCCGCCGCTTCACGCCGCCTTCCACCGCG
CTGAGCCCAGGCAAGATGAGCGAGGCGTTGCCG
CTGGGCGCCCCGGACGCCGGCGCTGCCCTGGCC
GGCAAGCTGAGGAGCGGCGACCGCAGCATGGTG
GAGGTGCTGGCCGACCACCCGGGCGAGCTGGTG
CGCACCGACAGCCCCAACTTCCTCTGCTCCGTG
CTGCCTACGCACTGGCGCTGCAACAAGACCCTG
CCCATCGCTTTCAAGGTGGTGGCCCTAGGGGAT
GTTCCAGATGGCACTCTGGTCACTGTGATGGCT
GGCAATGATGAAAACTACTCGGCTGACTGAGA
AATGCTACCGCAGCCATGAAGAACCAGGTTGCA
AGATTTAATGACCTCAGGTTTGTCGGTCGAAGT
GGAAGAGGGAAAAGCTTCACTCTGACCATCACT
GTCTTCACAAACCCACCGCAAGTCGCCACCTAC
CACAGAGCCATCAAAATCACAGTGGATGGGCCC
CGAGAACCTCGAAATCGTACTGAGAAGCACTCC
ACAATGCCAGACTCACCTGTGGATGTGAAGACG
CAATCTAGGCTGACTCCTCCAACAATGCCACCT
CCCCCAACTACTCAAGGAGCTCCAAGAACCCAGT
TCATTTACACCGACAACGTTAACTAATGGCACG
AGCCATTCTCCTACAGCCTTGAATGGCGCCCCC
TCACCACCCAATGGCTTCAGCAATGGGCCTTCC
TCTTCTTCCTCCTCCTCTCTGGCTAATCAACAG
CTGCCCCCAGCCTGTGGTGCCAGGCAACTCAGC
AAGCTGAAAAGGTTCCTTACTACCCTGCAGCAG
TTTGGCAATGACATTTCACCCGAGATAGGAGAA
AGAGTTCGCACCCTCGTTCTGGGACTAGTGAAC
TCCACTTTGACAATTGAAGAATTTCATTCCAAA
CTGCAAGAAGCTACTAACTTCCCACTGAGACCT
TTTGTCATCCCATTTTTGAAGGCCAACTTGCCC
CTGCTGCAGCGTGAGCTCCTCCACTGCGCAAGA
CTGGCCAAACAGAACCCTGCCCAGTACCTCGCC
CAGCATGAACAGCTGCTTCTGGATGCCAGCACC
ACCTCACCTGTTGACTCCTCAGAGCTGCTTCTC
GATGTGAACGAAACAGGAAGAGGCGAACTCCA
GACAGAACCAAAGAAAATGGCTTTGACAGAGAG
CCTTTGCACTCAGAACATCCAAGCAAGCGACCA
TGCACTATTAGCCCAGGCCAGCGGTACAGTCCA
AATAACGGCTTATCCTACCAGCCCAATGGCCTG
CCTCACCCTACCCCACCTCCACCTCAGCATTAC
CGTTTGGATGATATGGCCATTGCCCACCACTAC
AGGGACTCCTATCGACACCCCAGCCACAGGGAC
CTCAGGGACAGAAACAGACCTATGGGGTTGCAT
GGCACACGTCAAGAAGAAATGATTGATCACAGA
CTAACAGACAGAGAATGGGCAGAAGAGTGGAAA
CATCTTGACCATCTGTTAAACTGCATAATGGAC
ATGGTAGAAAAAACAAGGCGATCTCTCACCGTA
CTAAGGCGGTGTCAAGAAGCAGACCGGGAAGAA
TTGAATTACTGGATCCGGCGGTACAGTGACGCC
GAGGACTTAAAAAAAGGTGGCGGCAGTAGCAGC
AGCCACTCTAGGCAGCAGAGTCCCGTCAACCCA
GACCCAGTTGCACTAGACGCGCATCGGGAATTC
CTTCACAGGCCTGCGTCTGGATACGTGCCAGAG
GAGATCTGGAAGAAAGCTGAGGAGGCCGTCAAT
GAGGTGAAGCGCCAGGCGATGACGGAGCTGCAG
AAGGCCGTGTCTGAGGCGGAGCGGAAAGCCCAC
GACATGATCACAACAGAGAGGCCAAGATGGAG
CGCACGGTCGCCGAGGCCAAACGGCAGGCGGCG
GAGGACGCACTGGCAGTTATCAATCAGCAGGAG
GATTCAAGCGAGAGTTGCTGGAATTGTGGCCGT
AAAGCGAGTGAAACCTGCAGTGGCTGTAACACA
GCCCGATACTGTGGCTCATTTTGCCAGCACAAA
GACTGGGAGAAGCACCATCACATCTGTGGACAG
ACCCTGCAGGCCCAGCAGCAGGAACACACCT
GCAGTCAGCTCCTCTGTCACGCCCAACAGCGGG
GCTGGGAGCCCGATGGACACACCACCAGCAGCC
ACTCCGAGGTCAACCACCCCGGGAACCCCTTCC
ACCATAGAGCAAACCCCTCGCTAGACGTGAACT
CAGAACTGTCGGAGGAAAGACAACACAACCAAC
GCGAAACCAATTCCTCATCCTCAGATGCTCAAA
GTTGTTTTTTTGTTTGTTTGTTTATTAGATGA
ATTATCCTATTTCAGTACTTCAGCAAGAGAGAA
CCTAACTGTATCTTGAGGTGGTAGTAAAACACA

TABLE 2-continued

```
GAGGGCCAGTAACGGGTCGTAATGACTTATTGT
GGATAACAAAGATATCTTTTCTTTAGAGAACTG
AAAAGAGAGCAGAGAATATAACATGAAATGATA
GATTTGACCTCCTCCCTGTTATTTTCAAGTAGC
TGGGATTTTAAACTAGATGACCTCATTAACCGA
TGCTTTACCAAACAGCAAACCAAGAGATTGCTA
ATTGCTGTTGAAAGCAAAAATGCTAATATTAAA
AGTCACAATGTTCTTTATATACAATAATGG
(SEQ ID NO: 9)
```

In another embodiment, polynucleotides encoding an AML1-ETO protein can be generated by PCR amplification by selecting appropriate primers based on published sequences such as those above. Methods of PCR amplification, including the selection of primers, conditions for amplification, and cloning of the amplified fragments, are conventional. See, e.g., Innis, M. A. et al., eds. PCR Protocols: a guide to methods and applications, 1990, Academic Press, San Diego, Calif. and Wu et al., eds., Recombinant DNA Methodology, 1989, Academic Press, San Diego, Calif. In another embodiment, polynucleotide fragments encoding an AML1-ETO protein can be generated by chemical synthesis. Combinations of the above recombinant or non-recombinant methods, or other conventional methods, can also be employed.

Once a polynucleotide encoding an AML1-ETO protein or a fragment thereof has been isolated, it can be cloned into any of a variety of expression vectors, under the control of a variety of regulatory elements, and expressed in a variety of cell types and hosts, including prokaryotes, yeast, and mammalian, insect or plant cells, or in a transgenic, non-human animal.

A vector can include an AML1-ETO nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. Design of the expression vector can depend on such factors as choice of the host cell to be transformed, level of expression of protein desired, and the like. Expression vectors of the invention can be introduced into host cells to thereby produce proteins or polypeptides, including fusion proteins or polypeptides, encoded by nucleic acids as described herein (e.g., AML1-ETO proteins, mutant forms of AML1-ETO proteins, fusion proteins, and the like).

Examples of vectors that can be used include, for example, plasmids or modified viruses. Vectors are typically compatible with a given host cell into which they are introduced to facilitate vector replication and expression of an encoded reporter. Examples of specific vectors that may be useful in the practice of the present invention include, but are not limited to, E. coli bacteriophages, for example, lambda derivatives, or plasmids, for example, pBR322 derivatives or pUC plasmid derivatives; phage DNAs, e.g., numerous derivatives of phage 1, e.g., NM989, and other phage DNA, e.g., M13 and filamentous single stranded phage DNA; yeast vectors such as 2µ plasmids or derivatives thereof; vectors useful in eukaryotic cells, for example, vectors useful in insect cells, such as baculovirus vectors, vectors useful in mammalian cells such as retroviral vectors, for example pMIGR1, adenoviral vectors, adenovirus viral vectors, adeno-associated viral vectors, SV40 viral vectors, herpes simplex viral vectors and vaccinia viral vectors; vectors derived from combinations of plasmids and phage DNAs, plasmids that have been modified to employ phage DNA or other expression control sequences; and the like.

Methods of cloning nucleic acids are routine and conventional in the art. For general references describing methods of molecular biology which are mentioned in this application, e.g., isolating, cloning, modifying, labeling, manipulating, sequencing and otherwise treating or analyzing nucleic acids and/or proteins, see, e.g., Sambrook, J. et al. (1989). Molecular Cloning, a Laboratory Manual. Cold Harbor Laboratory Press, Cold Spring Harbor, N.Y.; Ausubel, F. M. et al. (1995). Current Protocols in Molecular Biology, N.Y., John Wiley & Sons; Davis et al. (1986), Basic Methods in Molecular Biology, Elsevir Sciences Publishing, Inc., New York; Hames et al. (1985), Nucleic Acid Hybridization, IL Press; Dracopoli, N. C. et al. Current Protocols in Human Genetics, John Wiley & Sons, Inc.; and Coligan, J. E., et al. Current Protocols in Protein Science, John Wiley & Sons, Inc.

AML1-ETO Acetylation

Histone modifying enzymes can regulate binding of specific chromatin-binding proteins to histone and also change affinity of histones for DNA (Choudhary, C. et al., Science 325, 834, 2009; Kouzarides, T., EMBO J 19, 1176, 2000). These enzymes also affect non-histone proteins, and post-translational modifications (PTM) of transcription factors like p53 or AML1 (which is required for definitive hematopoietic development) can regulate their protein-protein interactions, and their activity (Choudhary et al.; Kouzarides; Wang, L., Blood Cells Mol Dis. 43, 30, 2009). For instance, p300 binds to the C-terminus of AML1 and acetylates its N-terminus, promoting its activating function (Yamaguchi, Y. et al, J Biol Chem 279, 15630, 2004; Kitabayashi, I., et al, EMBO J 17, 2994, 1998). Interestingly, when AML1 is fused to ETO by the t(8;21), the p300 binding region of AML1 is lost from the AML1-ETO (A-E) fusion protein. Based on studies of hematopoietic development, and specific gene promoter function, A-E is generally considered to act as a transcription repressor, via recruitment of corepressors such as NCoR and SMRT (Nimer, S. D. et al., Oncogene 23, 4249, 2004; Wildonger, J, et al., Development 132, 2263, 2005; Minucci, S., et al, Oncogene 20, 3110, 2001). Although A-E also upregulates target gene expression (Frank, R. C. et al, Oncogene 18, 1701, 1999; Klampfer, L. et al, Proc Natl Acad Sci USA 93, 14059, 1996), information about mechanisms of gene activation and importance of the upregulated genes is sparse.

The invention described herein encompasses recognition that acetylation of AML1-ETO promotes transcriptional activation and cancer progression. In some embodiments, AML1-ETO is acetylated by a histone acetylase. In some embodiments, AML1-ETO is acetylated by p300. In some embodiments, AML1-ETO is acetylated on any lysine residue contained therein. In some embodiments, AML1-ETO is acetylated on K24 (SEQ ID NO: 1). In some embodiments, AML1-ETO is acetylated on K43 (SEQ ID NO: 1). In some embodiments, AML1-ETO is acetylated on K24 and K43 (SEQ ID NO: 1).

In some embodiments, acetylation of AML1-ETO is detected using immunological methods. In some embodiments, an antibody against acetylated AML1-ETO or fragments thereof is used to detect acetylated AML1-ETO. A number of methods for measuring antibody-antigen binding are known in the art, including ELISA (enzyme-linked immunosorbent assay), Western blotting, competition assay, immunoprecipitation, immunohistochemistry, and spot-blot. The detection step may be, for instance, chemiluminescent, fluorescent, or colorimetric.

In some embodiments, acetylation of AML1-ETO results in transcriptional activation of an AML1-ETO target gene. In some embodiments, transcription of an AML1-ETO target gene is activated 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, or 10,000 fold or more. In some embodiments, an AML1-ETO target gene is any gene that shows increased transcription in response to AML1-ETO acetylation. In some embodiments, an AML1-ETO target gene is Id1. In some embodiments, an AML1-ETO target gene is p21. In some embodiments, an AML1-ETO target gene is Egr1.

In some embodiments, transcriptional activation of an AML1-ETO target genes is detected by determining a level of RNA transcripts. Methods of quantifying levels of RNA transcripts are well known in the art and include but are not limited to northern analysis, semi-quantitative reverse transcriptase PCR, quantitative reverse transcriptase PCR, and microarray analysis. These and other basic RNA transcript detection procedures are described in Ausebel et al. (Ausubel F M, Brent R, Kingston R E, Moore D D, Seidman J G, Smith J A, Struhl K (eds). 1998. *Current Protocols in Molecular Biology*. Wiley: New York).

In some embodiments, transcriptional activation of an AML1-ETO target genes is detected by determining a level of a reporter gene. In some embodiments, an AML1-ETO target gene or fragment thereof is operably linked to a reporter on a reporter gene construct. In some embodiments, an AML1-ETO target gene promoter or fragment thereof is operably linked to a reporter on a reporter gene construct.

A reporter gene construct is a nucleic acid molecule that includes a nucleic acid encoding a reporter operatively linked to a transcriptional control sequences. Transcription of the reporter gene is controlled by these sequences. Activity of at least one or more of these control sequences is directly or indirectly regulated by transcription factors and other proteins or biomolecules. Transcriptional control sequences include a promoter and other regulatory regions, such as enhancer sequences, that modulate activity of the promoter, or control sequences that modulate activity or efficiency of RNA polymerase that recognizes the promoter, or control sequences are recognized by effector molecules. Such sequences are herein collectively referred to as transcriptional regulatory elements or sequences.

A reporter refers to any entity that allows for detection of a molecule of interest, such as a protein expressed by a cell, or a biological particle. Typical reporter entities include, include, for example, light emitting proteins such as luciferase, fluorescent proteins, such as red, blue and green fluorescent proteins (see, e.g., U.S. Pat. No. 6,232,107, which provides GFPs from *Renilla* species and other species), lacZ gene from *E. coli*, alkaline phosphatase, secreted embryonic alkaline phosphatase (SEAP), chloramphenicol acetyl transferase (CAT), hormones and cytokines and other such well-known genes. For expression in cells, nucleic acid encoding a reporter entity can be expressed as a fusion protein with a protein of interest or under control of a promoter of interest. Expression of these reporter genes can also be monitored by measuring levels of mRNA transcribed from these genes. Techniques for assessing activity level of enhancers using reporter genes are well known in the art. In some embodiments, reporter gene protein levels are assayed through ELISA, western blot, FACS, MACS, flow cytometry, β-galactosidase assays and/or immunohistochemistry.

Reporter gene constructs may be or include any vector that facilitates expression of a reporter sequence in a construct in a host cell. Any suitable vector can be used as described herein.

Test Agents

The present disclosure provides assays for screening for a test agent, or more typically, a library or collection of test agents, to evaluate an effect of the test agent on activity of or screened, for their effect on acetylation of AML1-ETO and/or AML1-ETO mediated transcriptional activation.

A test agent can be any chemical compound, for example, a macromolecule (e.g., a polypeptide, a protein complex, or a nucleic acid) or a small molecule (e.g., an amino acid, a nucleotide, or an organic or inorganic compound). The test agent can have a formula weight of less than about 10,000 grams per mole, less than 5,000 grams per mole, less than 1,000 grams per mole, or less than about 500 grams per mole, e.g., between 5,000 to 500 grams per mole. The test agent can be naturally occurring (e.g., a herb or a nature product), synthetic, or both. Examples of macromolecules are proteins (e.g., antibodies, antibody fragments), protein complexes, and glycoproteins, nucleic acids, e.g., DNA, RNA (e.g., siRNA), and PNA (peptide nucleic acid). Examples of small molecules are peptides, peptidomimetics (e.g., peptoids), amino acids, amino acid analogs, polynucleotides, polynucleotide analogs, nucleotides, nucleotide analogs, organic or inorganic compounds e.g., heteroorganic or organometallic compounds.

In certain embodiments, the test agent is an antibody or antibody fragment (e.g., diabody) directed to AML1-ETO protein. The antibody or antibody fragment may be directed to any region of the AML1-ETO protein. The antibody may be polyclonal or monoclonal. The antibody may be of any isotype. The antibody may be derived from any species; however, for use in humans, the antibody is typically of human origin or has been humanized. If the antibody is to be used in other species, the antibody may be adapted to that species. In certain embodiments, the antibody is a humanized monoclonal antibody. In certain specific embodiments, the antibody is a wholly human monoclonal antibody. Techniques for engineering and preparing antibodies are known in the art and are described in U.S. Pat. No. 4,816,567, issued Mar. 28, 1989; U.S. Pat. No. 5,078,998, issued Jan. 7, 1992; U.S. Pat. No. 5,091,513, issued Feb. 25, 1992; U.S. Pat. No. 5,225,539, issued Jul. 6, 1993; U.S. Pat. No. 5,585,089, issued Dec. 17, 1996; U.S. Pat. No. 5,693,761, issued Dec. 2, 1997; U.S. Pat. No. 5,693,762, issued Dec. 2, 1997; U.S. Pat. No. 5,869,619; issued 1991; U.S. Pat. No. 6,180,370, issued Jan. 30, 2001; U.S. Pat. No. 6,548,640, issued Apr. 15, 2003; U.S. Pat. No. 6,881,557, issued Apr. 19, 2005; U.S. Pat. No. 6,982,321, issued Jan. 3, 2006; incorporated herein by reference.

In certain other embodiments, the test agent may be a protein, peptide, or small molecule that mimics an antigen binding site of an antibody directed to an AML1-ETO protein. These agents may be designed or identified in silico based on the structure of the antigen binding site of the antibody directed to AML1-ETO protein. The agents may then be tested in various in vitro assays to assess the ability of the agent to inhibit AML1-ETO protein. The agents may also be identified using high-throughput screening methods using libraries of small molecules, peptides, or polynucleotides.

In certain embodiments, a test agent is a nucleic acid molecule, e.g., DNA or RNA. In some embodiments, a nucleic acid molecule mediates RNA interference. RNA interference refers to sequence-specific inhibition of gene expression and/or reduction in target RNA levels mediated by an at least partly double-stranded RNA, which RNA comprises a portion that is substantially complementary to a target RNA. Typically, at least part of the substantially complementary portion is within the double stranded region of the RNA. In some embodiments, RNAi can occur via selective intracellular degradation of RNA. In some embodiments, RNAi can occur by translational repression. In some embodiments, RNAi agents mediate inhibition of gene expression by causing degradation of target transcripts. In some embodiments, RNAi agents mediate inhibition of gene expression by inhibiting translation of target transcripts. Generally, an RNAi agent includes a portion that is substantially complementary to a target RNA. In some embodiments, RNAi agents are at least partly double-stranded. In some embodiments, RNAi agents are single-stranded. In some embodiments, exemplary RNAi agents can include small interfering RNA (siRNA), short hairpin RNA (shRNA), and/or microRNA (miRNA). In some embodiments, an agent that mediates RNAi includes a blunt-ended (i.e., without overhangs) dsRNA that can act as a Dicer substrate. For example, such an RNAi agent may comprise a blunt-ended dsRNA which is >25 base pairs length. RNAi mechanisms and the structure of various RNA molecules known to mediate RNAi, e.g. siRNA, shRNA, miRNA and their precursors, are described, e.g., in Dykxhhorn et al., 2003, Nat. Rev. Mol. Cell. Biol., 4:457; Hannon and Rossi, 2004, Nature, 431:3761; and Meister and Tuschl, 2004, Nature, 431:343; all of which are incorporated herein by reference.

In some embodiments, a test agent is the only substance assayed by a method described herein. In some embodiments, a collection of test agents are assayed either consecutively or concurrently by methods described herein. Members of a collection of test agents can be evaluated individually or in a pool, e.g., using a split-and-pool method.

In some embodiments, high throughput screening methods are used to screen a combinatorial chemical or peptide library, or other collection, containing a large number of potential test compounds. Such "combinatorial chemical libraries" are then screened in one or more assays to identify those library members (particular chemical species or subclasses) that display a desired characteristic activity. Compounds thus identified can serve as conventional "lead compounds" or can themselves be used as potential or actual modulators (e.g., as therapeutics).

A combinatorial chemical library typically includes a collection of diverse chemical compounds, for example, generated by either chemical synthesis or biological synthesis, by combining a number of chemical "building blocks" such as reagents. For example, a linear combinatorial chemical library such as a polypeptide library may be formed by combining a set of chemical building blocks (amino acids), e.g., in particular specified arrangements or in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like). Additional examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Some exemplary libraries are used to generate variants from a particular lead compound. One method includes generating a combinatorial library in which one or more functional groups of the lead compound are varied, e.g., by derivatization. Thus, the combinatorial library can include a class of compounds which have a common structural feature (e.g., scaffold or framework).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Test agents can also be obtained from: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) J. Med. Chem. 37:2678-85); spatially addressable parallel solid phase or solution phase libraries; synthetic library methods requiring deconvolution; the 'one-bead one-compound' library method; synthetic library methods using affinity chromatography selection, or any other source, including assemblage of sets of compounds having a structure and/or suspected activity of interest. Biological libraries include libraries of nucleic acids and libraries of proteins. Some nucleic acid libraries provide, for example, functional RNA and DNA molecules such as nucleic acid aptamers or ribozymes. A peptoid library can be made to include structures similar to a peptide library. (See also Lam (1997) Anticancer Drug Des. 12:145). A library of proteins may be produced by an expression library or a display library (e.g., a phage display library).

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner, U.S. Pat. No. 5,223, 409), spores (Ladner U.S. Pat. No. 5,223,409), plasmids (Cull et al. (1992) Proc Natl Acad Sci USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222:301-310; Ladner supra.).

Uses

Identifying Treatments

The present invention encompasses the recognition that the level of AML1-ETO acetylation corresponds to risk or incidence of AML and that AML1-ETO acetylation can be relied upon to identify new agents for inhibiting AML. As described herein, AML1-ETO is a major cause of AML, one of the most severe and treatment-resistant forms of leukemia. As such, there is a constant need for agents for treating and reducing risk of AML in patients with the t(8;21)(q22; q22) translocation.

In some embodiments, the current invention provides methods of identifying agents for treating or reducing risk for acute myelogenous leukemia comprising providing a system in which AML1-ETO acetylation level is determinable, contacting the system with a test agent, determining AML1-ETO acetylation level when the test agent is present, comparing the determined AML1-ETO acetylation level with a reference AML1-ETO acetylation level so that any difference between the reference level and the determined level is detected, and characterizing the test agent's usefulness in treating or reducing risk for acute myelogenous leukemia based on the detected difference.

In some embodiments, a system in which AML1-ETO acetylation level is determinable comprises any system comprising AML1-ETO. In some embodiments, a system is a system in which AML1-ETO acetylation occurs. In some embodiments, a system is a system in which AML1-ETO acetylation has occurred. In some embodiments, a system comprising AML1-ETO is an in vitro system. In some embodiments, an in vitro system comprises a cell free system. In some embodiments, an in vitro system comprises cell culture. In some embodiments, cell culture comprises cultured cells and cell culture media.

In some embodiments, cultured cells comprise any cell type capable of expressing AML1-ETO. In some embodiments, cultured cells comprise cells expressing AML1-ETO. In some embodiments, cultured cells comprise human cell lines. In some embodiments, cultured cells comprise mouse cell lines. In some embodiments, cultured cells comprise $CD34^+$ cells. In some embodiments, cultured cells comprise 293T cells. In some embodiments, cultured cells comprise HL60 cells. In some embodiments, cultured cells comprise MLA144 cells. In some embodiments, cultured cells comprise cells which do not express ETO. In some embodiments, cultured cells comprise Kasumi-1 cells. In some embodiments, cultured cells are cells transfected with a vector for expressing AML1-ETO as described herein. In some embodiments, cultured cells comprise cell lines derived from individuals with t(8;21)(q22;q22) translocations.

Techniques for culturing a wide variety of cell types are well known in the art. See, for example, Current Protocols in Molecular Biology (N.Y., John Wiley & Sons; Davis et al. 1986). Cell culture media utilized in accordance with the present invention is or comprises serum-free cell culture media. In certain embodiments, utilized cell culture media is fully defined synthetic cell culture media. In some embodiments, utilized cell culture media is Iscove's Modified Dulbecco's Medium (IMEM). In certain embodiments, utilized cell culture media is Dulbecco's Modified Eagle Medium (DMEM). In certain embodiments, utilized cell culture media is RPMI, Ham's F-12, or Mammary Epithelial Cell Growth Media (MEGM). In some embodiments, cell culture media comprises additional components including Fetal Bovine Serum (FBS), Bovine Serum (BS), and/or Glutamine or combinations thereof. In some embodiments, utilized media are supplemented with an antibiotic to prevent contamination. Useful antibiotics in such circumstances include, for example, penicillin, streptomycin, and/or gentamicin and combinations thereof. Those of skill in the art are familiar with parameters relevant to selection of appropriate cell culture media.

In some embodiments, a system comprising AML1-ETO is an in vivo system. In some embodiments, an in vivo system comprises an animal. In some embodiments, an animal comprises any animal commonly used for laboratory experiments, including but not limited to a rat, a dog, a non-human primate, a fly, a fish, a worm, a bird, a dog, a goat, or a mouse. Mouse models for AML expressing AML1-ETO are known in the art and include the AE9a mouse model, which expresses a truncated form of AML1-ETO known to induce leukemia (Yan, M. et al., Nat Med 2006;12:945-949) and MLL-AF9 mice, which express full length AML1-ETO (Dobson, C. L. et al., The EMBO Journal 1999, 18, 3564-3574).

In accordance with methods of the present invention, test agents are contacted with the system described herein. Methods of contacting test agents to in vitro and in vivo systems are well known in the art. Methods of contacting test agents to in vitro systems include, but are not limited to, pipeting, mixing, or any other means of transferring a solid or liquid into cell culture or a cell free system. Methods of contacting test agents to in vivo systems include, but are not limited to direct administration to a target tissue, such as heart or muscle (e.g., intramuscular), tumor (intratumorally), nervous system (e.g., direct injection into the brain; intraventricularly; intrathecally). Alternatively, test agents can be administered by inhalation, parenterally, subcutaneously, intradermally, transdermally, or transmucosally (e.g., orally or nasally). More than one route can be used concurrently, if desired.

In some embodiments, determining the AML1-ETO acetylation level when the test agent is present comprises methods for determining AML1-ETO acetylation described herein.

In some embodiments a reference AML1-ETO acetylation level is determined concurrently with the determined. In some embodiments a reference AML1-ETO acetylation level is determined concurrently with the determined AML1-ETO acetylation level. In some embodiments, a reference AML1-ETO acetylation level is determined historically relative to the determined AML1-ETO acetylation level. In some embodiments, a reference AML1-ETO acetylation level comprises the AML1-ETO acetylation level that is observed in the system or a comparable system under comparable conditions lacking the test agent. In some embodiments, a reference AML1-ETO acetylation level comprises the AML1-ETO acetylation level that is observed in the system or a comparable system under otherwise identical conditions lacking the test agent.

In some embodiments, a reference AML1-ETO acetylation level comprises the AML1-ETO acetylation level that is observed in the system or a comparable system under comparable conditions that include presence of a positive control agent. In some embodiments, a positive control agent comprises an agent characterized in that level of AML1-ETO acetylation is higher in an AML1-ETO acetylation system when that system is contacted with the agent than under otherwise identical conditions when the system is not so contacted with the agent.

In some embodiments, a reference AML1-ETO acetylation level comprises the AML1-ETO acetylation level that is observed in the system or a comparable system under comparable conditions that include presence of a negative control agent. In some embodiments, a negative control agent comprises an agent characterized in that level of AML1-ETO acetylation is lower in an AML1-ETO acetylation system when that system is contacted with the agent than under otherwise identical conditions when the system is not so contacted with the agent. In some embodiments, a negative control agent comprises Lys-CoA-Tat. In some embodiments, a negative control agent comprises C646.

In some embodiments, the current invention provides methods of identifying agents for treating or reducing risk for acute myelogenous leukemia comprising determining transcription levels of one or more targets of AML1-ETO transcriptional activation contacted to a test agent and identifying the test agent as treating or reducing risk for acute myelogenous leukemia if the transcription levels are reduced relative to transcription levels in comparable conditions lacking the test agent.

Treatments for AML

The present invention encompasses the recognition that modulation AML1-ETO acetylation represents an effective therapy and preventative treatment for AML caused by t(8;21)(q22;q22) translocations. In some embodiments, the current invention provides methods of treating or reducing risk for acute myelogenous leukemia comprising administering to a subject one or more AML1-ETO acetylation inhibitors. In some embodiments, the current invention provides methods of treating or reducing risk for acute myelogenous leukemia comprising administering to a subject one or more agents characterized in that transcription levels of one or more targets of AML1-ETO transcriptional activation are lower in the agent's presence as compared with in its absence.

In some embodiments, AML1-ETO acetylation inhibitors comprise agents characterized in that level of AML1-ETO acetylation is lower in an AML1-ETO acetylation system when that system is contacted with the agent than under otherwise identical conditions when the system is not so contacted with the agent.

In some embodiments, a subject is any mammalian subject at risk for a AML. In some embodiments, the subject is a human. In certain embodiments, the subject has a t(8;21)(q22;q22) translocation. In some embodiments, the subject has previously suffered from leukemia. In some embodiments, the subject is currently suffering from AML.

In accordance with the methods of the invention, an agent described herein can be administered to a subject alone, or as a component of a composition or medicament (e.g., in the manufacture of a medicament for the prevention or treatment of AML), as described herein. The compositions can be formulated with a physiologically acceptable carrier or excipient to prepare a pharmaceutical composition. The carrier and composition can be sterile. The formulation should suit the mode of administration. Methods of formulating compositions are known in the art (see, e.g., Remington's Pharmaceuticals Sciences, 17$^{th}$ Edition, Mack Publishing Co., (Alfonso R. Gennaro, editor) (1989)).

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulations can include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

An agent described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

An agent described herein (or a composition or medicament containing an agent described herein) is administered by any appropriate route. In some embodiments, an agent is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, an agent is administered intravenously. In some embodiments, an agent is administered orally. In other embodiments, an agent is administered by direct administration to a target tissue, such as heart or muscle (e.g., intramuscular), tumor (intratumorallly), nervous system (e.g., direct injection into the brain; intraventricularly; intrathecally). Alternatively, an agent (or a composition or medicament containing an agent) can be administered by inhalation, parenterally, intradermally, transdermally, or transmucosally (e.g., orally or nasally). More than one route can be used concurrently, if desired.

In some embodiments, a composition is administered in a therapeutically effective amount and/or according to a dosing regimen that is correlated with a particular desired outcome (e.g., with treating or reducing risk for AML).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, or combinations thereof). Such doses or amounts can be determined by those of ordinary skill In some embodiments, an appropriate dose or amount is determined in accordance with standard clinical techniques. Alternatively or additionally, in some embodiments, an appropriate dose or amount is determined through use of one or more in vitro or in vivo assays to help identify desirable or optimal dosage ranges or amounts to be administered.

In various embodiments, an agent is administered at a therapeutically effective amount. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of AML.

In some embodiments, provided compositions, including those provided as pharmaceutical formulations, comprise a liquid carrier such as but not limited to water, saline, phosphate buffered saline, Ringer's solution, dextrose solution, serum-containing solutions, Hank's solution, other aqueous physiologically balanced solutions, oils, esters and glycols.

In some embodiments, a formulation comprising an agent described herein administered as a single dose. In some embodiments, a formulation comprising an agent described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising an agent described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising an agent described herein is administered at regular intervals indefinitely. In some embodiments, a formulation comprising an agent described herein is administered at regular intervals for a defined period. In some embodiments, a formulation comprising an agent described herein is administered at regular intervals for 5 years, 4, years, 3, years, 2, years, 1 year, 11 months, 10 months, 9 months, 8 months, 7 months, 6 months, 5 months, 4 months, 3 months, 2 months, a month, 3 weeks, 2, weeks, a week, 6 days, 5 days, 4 days, 3 days, 2 days or a day.

Combination Therapy

In some embodiments, an agent is administered in combination with one or more known therapeutic agents (e.g., chemotherapeutic agents) currently used for AML prophylaxis and treatment. In some embodiments, the known therapeutic agent(s) is/are administered according to its standard or approved dosing regimen and/or schedule. In some embodiments, the known therapeutic agent(s) is/are administered according to a regimen that is altered as compared with its standard or approved dosing regimen and/or schedule. In some embodiments, such an altered regimen differs from the standard or approved dosing regimen in that one or more unit doses is altered (e.g., reduced or increased) in amount, and/or in that dosing is altered in frequency (e.g., in that one or more intervals between unit doses is expanded, resulting in lower frequency, or is reduced, resulting in higher frequency).

Traditional therapies or anticancer agents include surgery, radiotherapy (γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. Any and all of these therapies may be used in connection with the present invention.

EXEMPLIFICATION

Example 1

The Leukemogenicity of AML1-ETO is Dependent on Site-Specific Lysine Acetylation

Materials and Methods
Plasmid Construction

AML1-ETO or ETO constructs lacking amino acids 245-436 (the NHR1 domain plus some more C terminal amino acids) or amino acids 481 to 547 (the NHR2 domain) and the HA-AML1-ETOARunt construct lacking amino acids 48 to 182 were used. AML1-ETO and AML1-ETO9a constructs containing K24R, K43R or K24, 43R mutations were made using a PCR primer-directed mutagenesis kit (Stratagene), and a Flag-tag or HA-tag was added to their 5' end. All constructs were subcloned into the MIGR1 plasmid which possesses an IRES-GFP sequence. The BosNeo-p300 plasmid was used for IP experiments. The pLKO.1 plasmids expressing shRNA against human p300 were purchased from Open Biosystems, whereas control shRNA (scrambled shRNA) was purchased from Addgene.

Retroviral Production, Cord Blood Cell Transduction and Cell Culture

To produce retroviruses capable of expressing one of the AE proteins, the above MIGR1 plasmids were transiently transfected with the si-Ampho packaging vector into 293T cells using a calcium phosphate technique. Human cord blood samples were obtained through the Cord Blood Program of the New York Blood Center. CD34$^+$ cells were selected using the MACS CD34 isolation kit from Miltenyi Biotec (Auburn). Purified CD34$^+$ cells were then cultured for 72 hours in IMDM with 20% BIT 9500 (Stem Cell Technologies, Vancouver) and cytokine mix (FLT3 ligand 100 ng/mL; SCF 100 ng/mL; TPO 100 ng/mL; IL-6 20 ng/mL—all from Peprotech, Rocky Hill or ebioscience, San Diego). Following expansion in the culture medium, cord blood cells were transduced with retrovirus by spinoculation. Seventy two hours following their transduction, the cells were stained with an APC-conjugated anti-CD34 antibody (Becton Dickinson, San Jose), and the GFP$^+$/CD34$^+$ cells were sorted using MoFlo. The cells were counted and re-plated weekly at a concentration of $1 \times 10^5$/ml. To monitor erythroid differentiation, CD34$^+$ cells were grown in IMDM/BIT with SCF 100 ng/ml and EPO 6 units/ml. To monitor myeloid differentiation, CD34$^+$ cells were grown in IMDM/BIT with SCF 100 ng/ml, Flt3-L 10 ng/mL, IL-6 20 ng/ml, IL-3 20 ng/ml, GM-CSF 20 ng/mL and G-CSF 20 ng/mL.

Cobblestone Area Forming Cell (CAFC) Assay

To assay for stem cells using the CAFC assay, GFP$^+$ CD34$^+$ cells were cocultured on an MS-5 monolayer in IMDM containing 12.5% FCS, 12.5% horse serum, 1 µM hydrocortisone, 4 mM L-glutamine, and 100 U/ml penicillin/streptomycin. The cultures were demidepopulated each week. After 5 weeks in culture, total cobblestone areas were counted.

Flow Cytometry

To monitor CD34 expression, cells were stained with an APC-conjugated anti-CD34 antibody (Becton Dickinson). To monitor Glycophorin A and CD71 expression, cells were stained with a PE-conjugated anti-Glycophorin A antibody and an APC-conjugated anti-CD71 antibody (Beckman-Coulter). To monitor CD11b expression, cells were stained with a PE-conjugated anti-CD11b antibody (Beckman-Coulter). To monitor C-kit, CD45 and CD45.2 expression, cells were stained with APC-conjugated anti-C-kit, PE-conjugated anti-CD45 and PE-conjugated anti-CD45.2 antibody (Becton Dickinson). Data were analyzed with Flowjo software using a Becton Dickinson FACSCalibur.

Microarray Analysis

RNA was isolated from human CD34$^+$ cells expressing empty vector MIGR1, AML1-ETO or AML1-ETOΔNHR1 (aa245-436) using the Qiagen RNeasy Plus® mini kit, transcribed into cDNA using random hexamer priming and Superscriptase (Invitrogen), and then hybridized to the Affymetrix HG-U133 GeneChips. The data were analyzed using Partek Genomic Suites, version 6.5 to identify differentially expressed genes. Triplicate samples were prepared independently for each condition.

Real Time RT-PCR

The RNA extraction and cDNA generation procedures were described above. The reverse transcription reaction was performed for 10 min at 25° C., 50 min at 50° C., 5 min at 85° C. and 20 min at 37° C. Real-time quantitative PCR was performed using a TaqMan 7500 sequence detector system (Applied Biosystems). The thermal cycle conditions were:

50° C. for 2 min, 95° C. for 10 min to activate Amplitaq Gold DNA polymerase, denaturation at 95° C. for 15 seconds and anneal/extension at 60° C. for 1 min (45 cycles). Quantitative PCR for HPRT was performed to normalize for cDNA loading. The relative quantification of gene expression was calculated using the method ($2^{-C_t}$), as described by the manufacturer.

Luciferase Reporter Gene Assay

To assess GM-CSF and IL-3 promoter activity, MLA144 cells were transfected with either a pGL3-GM-CSF or a pGL3-IL-3 promoter-luciferase construct, with pRL-SV40 Renilla luciferase plasmid, and either the empty pcDNA3 vector, pcDNA3-AML1b, pcDNA3-AML1-ETO or pcDNA3-AML1-ETO-ΔNHR1(aa245-436) using the Amaxa electroporation nucleofector system (Amaxa Biosystems). Luciferase assays were carried out using the Dual-luciferase reporter assay system (Promega), and luminometric units were determined using the BioTek Synergy 2 plate reader (BioTek). To assess M-CSFR promoter activity, Hela cells were transiently transfected using the FuGene6 reagent (Roche). These transfections included the M-CSFR promoter-luciferase construct, the Renilla luciferase construct and pcDNA3/pcDNA3-AML1b and either MIGR1, MIGR1-AML1-ETO or MIGR1-AML1-ETO-ΔNHR1 (aa245-436). Luciferase promoter assays were performed as described above, and Renilla luciferase activity used to normalize transfection efficiency.

Antibodies

Anti-p300 (Millipore or Santa Cruz), anti-Flag (Sigma), anti-HA (Santa Cruz), anti-ETO (generated in the Roeder lab or Santa Cruz), anti-AML1 (Zhao, X. et al, Genes Dev 22, 640, 2008), anti-acetylated lysine (Stressgen), anti-acetylated Histone H3 (Millipore), anti-Tubulin (Sigma), anti-TAFII250 (generated in the Roeder lab) and anti-TAF7 (generated in the Roeder lab) antibodies were used. Two anti-acetylated AML1-ETO polyclonal antibodies were generated by immunizing rabbits with the synthetic peptides (TALSPGK [acetylated] MSEA SEQ ID NO: 10 or LAGK [acetylated] LRSGDRS SEQ ID NO: 11) conjugated to KLH. The polyclonal antiserum was collected and purified using a peptide affinity column. The affinity of the antibodies against acetyl-lysine AML1-ETO was measured by dot blot assays. For the dot blot assays, 5 pmol of peptide (measured by Ellman's reagent) was spotted onto a nitrocellulose membrane. The control peptides were as follows: AML1-

ETOK24 peptide (TALSPGKMSEA) (SEQ ID NO: 10) and AML1-ETOK43 peptide (LAGK LRSGDRS) (SEQ ID NO: 11).

Immunoprecipitation and Western Blot Assays

The Flag-AE, Flag-AE-ΔNHR1 (aa245-436), Flag-AE-ΔNHR2, Flag-ETO, Flag-ETO-ΔNHR1 and Flag-ETO-ΔNHR2 cDNAs were cotransfected into 80% confluent 293T cells using the FuGene 6 reagent. After 36 hours the cells were lysed in RIPA buffer with 1 mM DTT and DNAse I 1 µg/mL and a proteinase inhibitor cocktail (Roche), and incubated on ice for 30 minutes. Nuclear extracts were prepared to examine the endogenous protein-protein interactions. Anti-Flag agarose (Sigma), anti-HA agarose (Pierce) or protein A/G agarose (Santa Cruz) was used in the immunoprecipitation assays. For western blot assays, protein samples were separated by electrophoresis on denaturing 3-8% or 4-12% premade polyacrylamide gels (Invitrogen) and blotted to PVDF membranes (Millipore).

Chromatin Immunoprecipitation (ChIP) Assays

Chromatin immunoprecipitation assays were performed using an antigen-purified anti-ETO antibody and a p300 antibody (Santa Cruz). $8 \times 10^7$ Kasumi-1 cells were used for each ChIP reaction. Kasumi-1 cells (which do not express ETO protein) were first dual cross-linked with 2 mM Disuccinimidyl glutarate and 1% formaldehyde and then lysed with buffer (1% SDS, 10 mM EDTA, 50 mM Tris-HCl, pH 8.1). The cell lysates were subjected to sonication, diluted in buffer (0.01% SDS, 1.1% Triton X-100, 1.2 mM EDTA, 16.7 mM Tris-HCl, pH 8.1, 167 mM NaCl) and then immunoprecipitated using the indicated antibodies. Subsequently, the immunoprecipiated DNA was purified, and quantified by Real-Time PCR at specific genomic loci within the genes of interest. Quantitative results are represented as percentages of the total input. ChIP-seq libraries were constructed following the Illumina protocol. Briefly, end-repair, "A" addition, and adaptor ligation were performed on 10 ng ChIP or Input DNA. Adaptor-ligated DNA with a size between 200 to 300 bp was selected and amplified to generate a DNA library suitable for sequencing. 8 µM of the sequencing library was applied to Illumina Single-Read flowcells for cluster generation on cBot. Finally, the clusters were sequenced on the Illumina Genome Analyzer II to generate 36-bp short sequence reads, which were aligned to the human reference genome (hg18) using ELAND. After filtering clonal reads, uniquely aligned reads were then used to perform peak-calling by ChIPseeqer (icb.med.cornell.edu/wiki/index.php/Elementolab/).

Fetal Liver Transplantation

Fetal liver cells were harvested from E14.5 embryos. Subsequently, LSK (Lin$^-$, Sca1$^+$, C-kit$^+$) cells were sorted and infected with retroviruses by spinoculation. The fetal liver HSPCs were cultured in X-VIVO medium with 10 ng/ml IL-3, 10 ng/ml IL-6 and 100 ng/ml stem cell factor (Peprotech). The efficiency of transduction by the various MIGR1-based viruses was determined on the basis of GFP positivity using flow cytometry. The C57Bl/6.SJL recipient mice were lethally irradiated with 950 cGy, given in a split dose separated by 4 hours. The transduced fetal liver cells were transplanted into recipient mice by tail-vein injection.

Knocking Down p300 in the t(8;21)$^+$ Kasumi-1 Leukemia Cell Line

The lentivirus expressing shRNAs against p300, or a control shRNA (scrambled shRNA), was produced in 293T cells. To stably knock down the expression of p300 in Kasumi-1 cells, 1 µg/ml puromycin (Sigma) was used to select the positive clones. 72 hours after the puromycin selection, RNA and protein were collected for the Q-PCR and Western blotting experiments.

Lys-CoA-Tat or C646 Treatment of Primary Leukemia Cells and Leukemia Cell Lines

Leukemia cells were obtained from two AML patients with t(8;21) by Ficoll-hypaque separation. Informed consent was obtained from the patients, according to institutional (IRB) guidelines. The cell viabilities of the primary leukemia cells, Kasumi-1 cells, HL60 cells and human CD34$^+$ cells were assessed by triplicate counting of trypan blue dye-excluding cells under light microscopy. The cell morphology was evaluated by Wright's staining of cells prepared by cytospin centrifugation. Blast cells were isolated from the bone marrow and spleen of the mice with AE9a or MLL-AF9 driven leukemia, and treated for 12 hours with Lys-CoA-Tat or DDDD-Tat (at 50 µM), or C646 vs. C37 (at 20 µM). Female C57Bl/6 mice were sublethally irradiated with 475 cGy, and then injected with $3 \times 10^6$ treated blast cells via tail vein.

Peptide Pull-down Assays

Acetylated and nonacetylated peptides (used for antibody development) were conjugated to SulfoLink agarose (Pierce). For each pull-down reaction, 100 µg of nuclear extract from K562 cells were used with 10 µg of peptide-bound beads in the binding buffer (150 mM NaCl and 20 mM HEPES pH 7.9). After rotating overnight at 4° C., the beads were washed five times with binding buffer, and five times with 300 mM NaCl and 20 mM HEPES (pH 7.9) buffer, plus protease inhibitors. The bound protein was then eluted with 500 mM NaCl and 20 mM HEPES (pH 7.9) buffer, and analyzed by Western blot analysis.

Electrophoretic Mobility Shift Assays (EMSA)

N-terminal Flag-tagged AE, AEK24R, AEK43R or AEK24,43R proteins were prepared as nuclear extracts from 293T cells transfected with each expression construct, using the empty vector MIGR1 as a control. The oligonucleotide probes contained sequences from the human separase gene; wild type (Wt): (5'-GAGTGGTGTGGTAGTGCG-GTCGGGG-3') (SEQ ID NO: 12) or the AML1 binding site mutant (Mu) (5'-GAGTGGTGTGGTAGT-GCTAGCGGGG-3') (SEQ ID NO: 13). The Wt seperase probe was labeled with biotin. The incubation mixtures were separated by 6% non-denaturing PAGE gel and the bands were detected by LightShift Chemiluminescent EMSA Kit (Pierce).

MTT Reduction Assay

Cells were treated with p300 inhibitors at different concentrations in a 96-well plate. After 72 hours, 0.1 mg MTT was added to each well. The samples were incubated at 37° C. for 4 hours and the absorbance was measured at 570 nm by spectrophotometry.

Statistical Analysis

Assays were set up in triplicates and the results expressed as the mean±SD. Statistical analyses were performed using Student's t-test. Survival functions were estimated using the Kaplan-Meier method and compared by the log-rank test.

Results

The NHR1 domain in A-E binds HEB, a class I basic helix-loop-helix protein (i.e. an E protein) (Zhang, J. et al, Science 305, 1286, 2004). To understand the importance of this domain to the leukemia-promoting properties of A-E, the effects of "wild type" A-E with the A-EΔNHR1 construct (which lacks aa245-436) on the self-renewal and differentiation potential of human CD34$^+$ hematopoietic stem/progenitor cells (HSPC) isolated from cord blood (CB) was compared.

Figure 2:
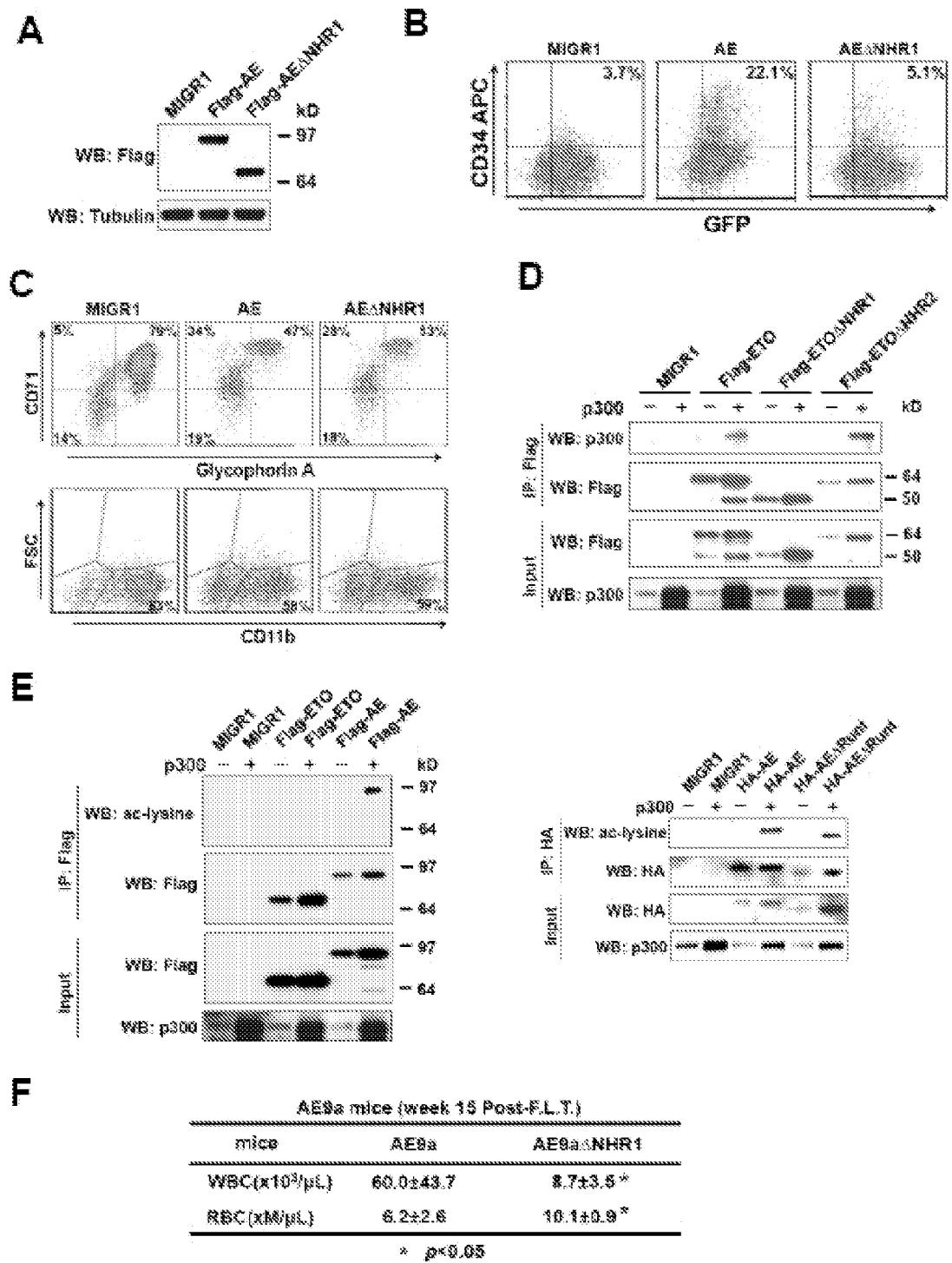
FIGS. 2A-2F shows Loss of NHR1 domain does not affect AML1-ETO induced block in erythroid/myeloid differentiation. (A) NHR1 domain deletion in AML1-ETO does not affect its expression level in human CD34$^+$ cells. Human CD34$^+$ cells transduced with MIGR1 empty vector, Flag-AE or Flag-AEΔNHR1 were analyzed; an anti-Flag antibody and anti-tubulin antibody were used for Western blotting. (B) Deletion of NHR1 affects ability of AML1-ETO to promote self-renewal in liquid culture assays. Representative percentages of CD34$^+$ GFP$^+$ cells at week 3 are shown. (C) Inhibition of erythroid differentiation and myeloid differentiation is seen with human CD34$^+$ cells expressing either AE or AEΔNHR1. Glycophorin A and CD71 expression was examined in cells grown in liquid culture with erythroid differentiation-driving cytokines on Day 11; a representative experiment is shown (top panels). CD11b expression was examined in cells growing in liquid culture with myeloid differentiation-driving cytokines on Day 9; a representative experiment is shown (bottom panels). (D) The NHR1 domain is required for interaction of ETO with p300. An anti-Flag antibody was used for IP, and an anti-p300 or anti-Flag antibody for Western blotting. (E) AML1-ETO is acetylated by p300 at its N terminus. Flag-tagged AE or ETO and p300 were co-transfected into 293T cells (left panel). HA-tagged AE or AEΔRunt and p300 were also co-transfected into 293T cells (right panel). An anti-Flag antibody or anti-HA antibody was used for IP, and anti-acetylated lysine, anti-Flag, anti-HA and anti-p300 antibodies were used for Western blotting. (F) Lethally irradiated recipient mice were injected with fetal liver cells transduced with AE9a or AE9aΔNHR1. WBC and RBC of these mice are shown 15 weeks post-transplant (±SD; n=5).

After confirming the expression of Flag-tagged A-E and A-EΔNHR1 by Western blotting (FIG. 2A), HSPC self-renewal using CAFC (cobblestone area-forming cell) assays was examined (Mulloy, J. C. et al, *Blood* 99, 15, 2002; Mulloy, J. C., et al, *Blood* 102, 4369, 2003). Unlike A-E, A-EΔNHR1 did not increase the number of CAFC present at week 5 (FIGS. 1A and 3C), nor did it promote the maintenance of CD34$^+$ HSPCs growing in liquid culture (5.1% for A-EΔNHR1 vs 22.1% for A-E, and 3.7% for the MIGR1 control). The results presented herein indicate an essential role for the NHR1 (aa245-436) domain in the self-renewal promoting effects of A-E in this model (FIGS. 1B and 2B).

To define whether the NHR1 domain is required for the inhibitory effect of A-E on differentiation, A-EΔNHR1 transduced cells were grown in liquid culture with erythroid- or myeloid-differentiation-promoting cytokines for 9 days. Both the A-E and the A-EΔNHR1 expressing cells showed a similar decrease in Glycophorin A, CD71 and CD11b expression (FIG. 2C). The results presented herein suggest loss of the NHR1 domain affects the self-renewal signals provided by A-E, but not the delay (or block) in myelo-erythroid differentiation.

Figure 3:
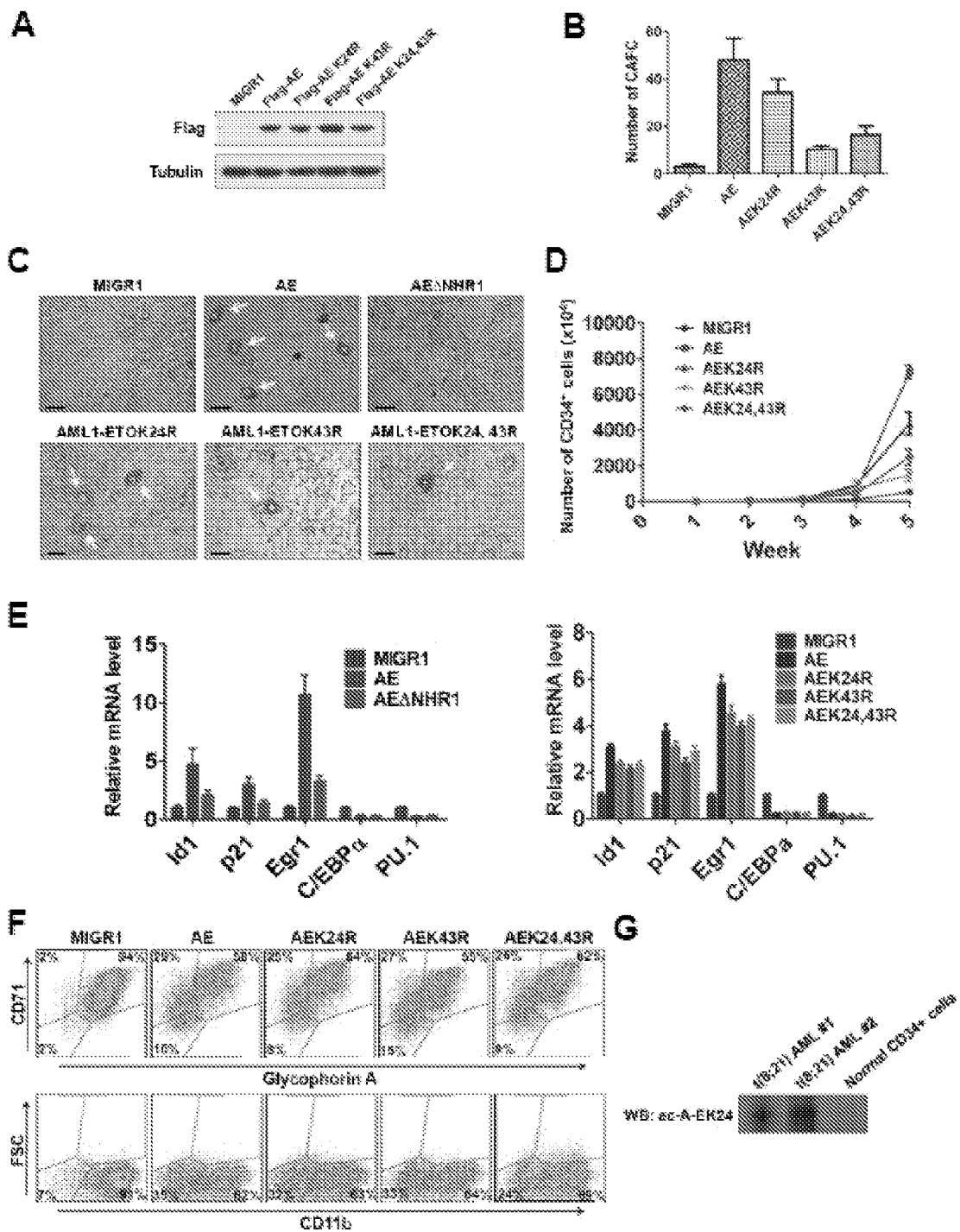
FIGS. 3A-3G show mutation of K43 to R in AML1-ETO abrogated its self-renewal promoting capacity but had no effect on its block of myeloid/erythroid differentiation in CD34$^+$ cells. (A) Mutation of K24R, K43R or K24, 43R in AML1-ETO does not affect its expression level in human CD34$^+$ cells. Human CD34$^+$ cells transduced with MIGR1 empty vector, Flag-AE, Flag-AEK24R, Flag-AEK43R or Flag-AEK24,43R were analyzed. An anti-Flag antibody and anti-tubulin antibody were used for Western blotting. (B and C) Deletion of NHR1 or mutation of K43 in AML1-ETO affects its ability to promote self-renewal. MIGR1, AE, AEΔNHR1, AEK24R, AEK43R or AEK24, 43R transduced human CD34 cells were plated on MS-5 stromal cells, and triplicate flasks examined for number of cobblestone areas after 5 weeks. Cobblestone areas are indicated by white arrows (scale bar: 25 μM). (D) Mutation of K43R affects ability of AML1-ETO to promote self-renewal in liquid culture assays. Growth of human CD34$^+$ AE, AEK24R, AEK43R and AEK24, 43R transduced cells was examined weekly and plotted (±SD; n=3). (E) Upregulation of AML1-ETO target genes is affected by deletion of the NHR1 domain or mutation at AML1-ETOK43. Total RNA was extracted from CD34$^+$ cells transduced with MIGR1, AE, AEΔNHR1, AEK24R, AEK43R or AEK24, 43R and mRNA levels of AML1-ETO target genes was examined by Q-PCR (±SD; n=3). (F) CD34$^+$ cells expressing AE, AEK24R, AEK43R or AEK24, 43R all show a block in erythroid and myeloid differentiation. Glycophorin A and CD71 expression was measured on cells growing in liquid culture with erythroid differentiation-driving cytokines on Day 11; a representative experiment is shown (top panels). CD11b expression on cells was examined in liquid culture with myeloid differentiation-driving cytokines on Day 9; a representative experiment is shown (bottom panels). (G) Acetylation of A-EK24 can be detected in blast cells isolated from t(8;21)$^+$ leukemia patients. Anti-ETO antibody was used for IP, and anti-acetyl A-EK24 was used for Western blotting.

To gain insight into how the NHR1 domain of A-E promotes self-renewal, microarray-based expression assays were used to compare transcriptomes of the A-E and A-EΔNHR1-transduced human HSPCs (vs control MIGR1-transduced HSPCs). Several potential regulators of HSC self-renewal (Id1, p21 and Egr1) were upregulated by A-E but not by A-EΔNHR1 (Jankovic, V. et al, *Proc Natl Acad Sci USA* 104, 1260, 2007; Viale, A. et al, *Nature* 457, 51, 2009; Wilson, A. et al., *Curr Opin Genet Dev* 19, 461, 2009) (FIG. 3E). Similarly, A-EΔNHR1 was much less transactivating than A-E on the M-CSFR promoter (FIG. 1C) (Rhoades, K. L., et al, *Proc Natl Acad Sci USA* 93, 11895, 1996). In contrast, the differentiation-promoting genes, c/EBPα and PU.1, that are downregulated by A-E are still downregulated by A-EΔNHR1 (Frank, R. et al, *Oncogene* 11, 2667, 1995; Uchida, H. et al., *J Immunol* 158, 2251, 1997) (FIG. 3E), and both the IL-3 and GM-CSF promoters were similarly downregulated by A-E and A-EΔNHR1 (FIG. 1C). The results presented herein suggest that the NHR1 domain is required for transcriptional activation but not repression by A-E, and for its effects on self-renewal, but not differentiation.

Figure 4:
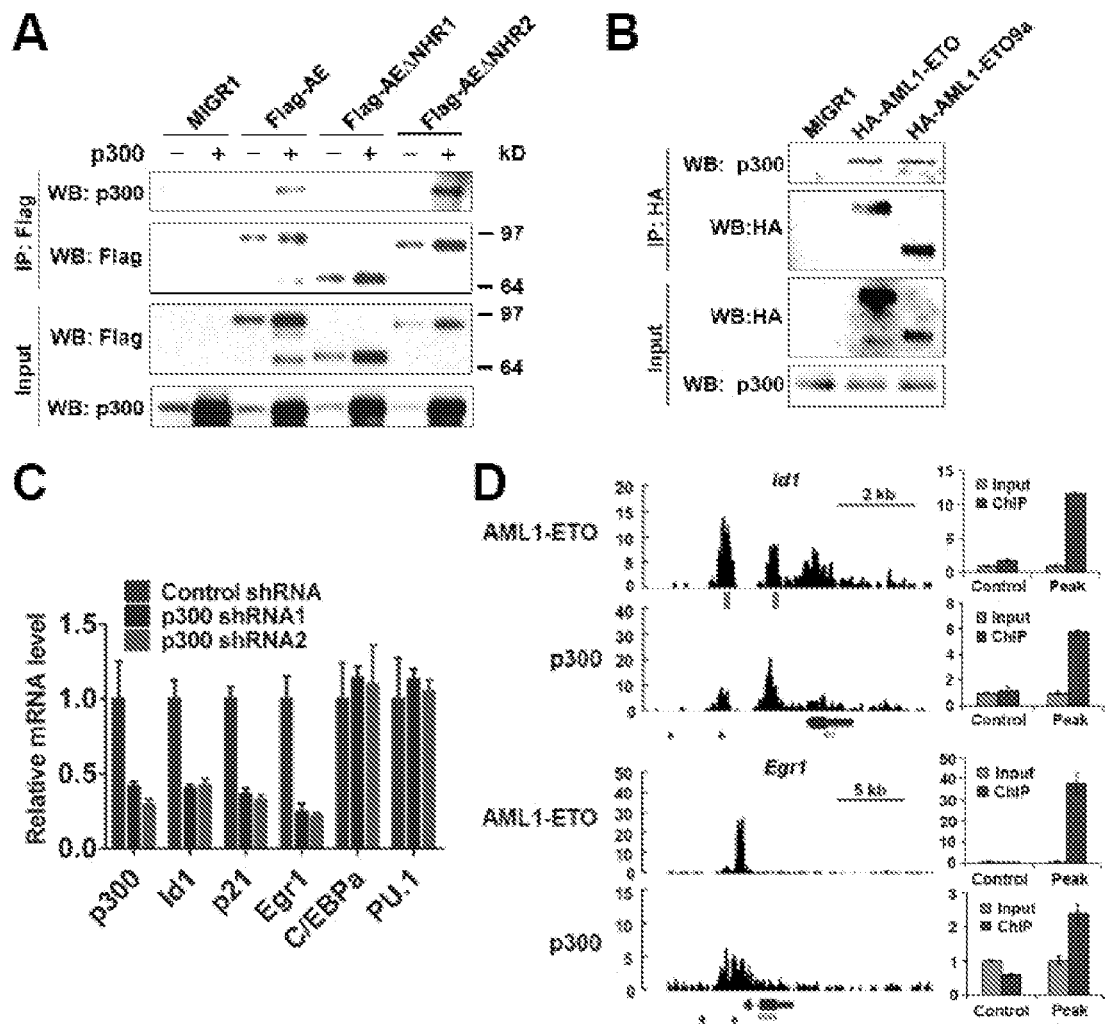
FIGS. 4A-4D shows the NHR1 domain of A-E interacts with p300, which potentiates its transcriptional activating properties. (A) The NHR1 domain is required for interaction of A-E with p300. An anti-Flag antibody was used for IP, and anti-p300 or anti-Flag antibodies for Western blotting. (B) A-E9a also interacts with p300. An anti-HA antibody was used for IP, and anti-p300 or HA antibodies were used for Western blotting. (C) Knock down of p300 decreased expression of A-E activated target genes. Kasumi-1 cells were transduced with shRNAs against p300 or a control shRNA. Q-PCR was performed to quantify the level of target gene expression (±SD; n=3). (D) A-E and p300 co-localize on some A-E upregulated genes, as shown by ChIP-seq assays. Representative examples of A-E and p300 co-occupancy are shown, as custom tracks in the UCSC genome browser. Locations of Runx1 consensus binding sites are shown by vertical lines, on the x axis. DNA binding was also analyzed by Q-PCR amplification of regions indicated by arrows on the x axis (±SD; n=3).
Figure 10:
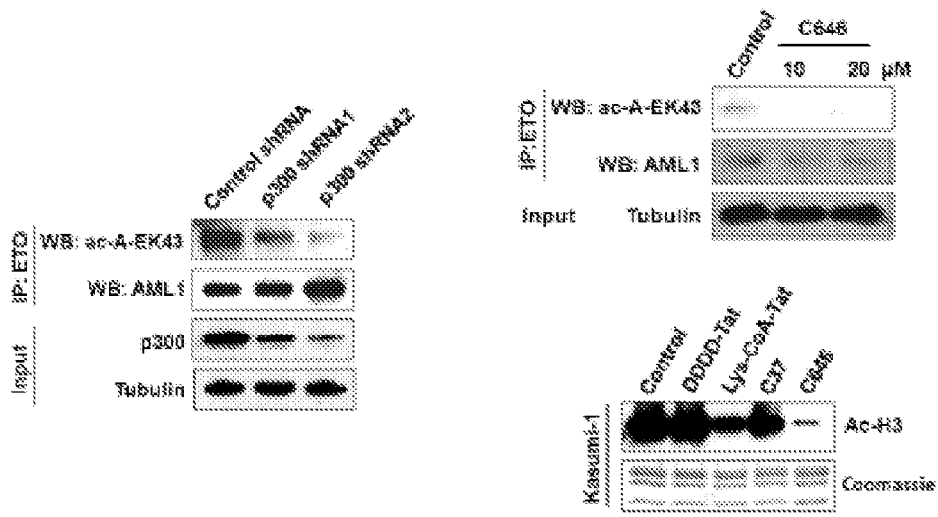
FIGS. 10A-10D shows effects of p300 inhibition on various AML cell lines. (A) Knockdown or inhibition of p300 decreased acetylation of AML1-ETO on K43. Kasumi-1 cells were transduced with two shRNAs directed against human p300, or a control shRNA (left panel). After 3 days of puromycin selection, IP and Western blotting were performed as in FIG. 9B. Kasumi-1 cells were treated with C646 (10 or 20 µM) for 24 hours, and acetylation of AML1-ETO and Histone H3 was analyzed as described (right panel). (B) AML1-ETO interacts with p300 in vitro and in vivo. Purified AML1-ETO and p300 were used for in vitro binding assays (left panel). Nuclear extracts of Kasumi-1 cells were subjected to IP with an anti-ETO antibody; anti-p300 or anti-AML1 antibodies were used for Western blotting (right panel). (C) Inhibitory effects of Lys-CoA-Tat (50 µM) and C646 (5 µM) on growth of AML cell lines was measured using the MTT assay, after 72 hours of treatment (±SD; n=3). (D) C646 downregulated expression of AML1-ETO activated target genes at 24 hours. Kasumi1 cells were treated with 20 µM C646 for 24 hours, and RNA was collected to measure Id1, p21, Egr1, C/EBPα and PU.1 mRNA levels using qPCR (±SD; n=3).
Figure 10:
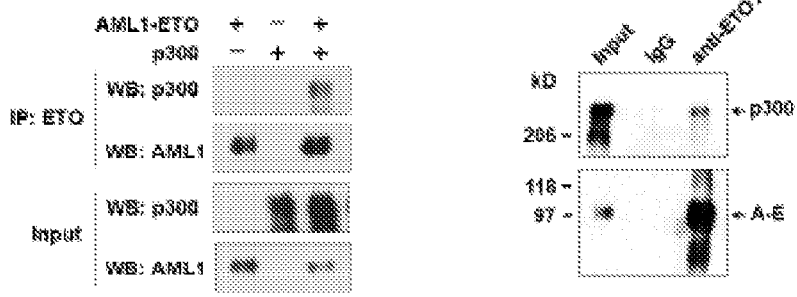
Figure 10:
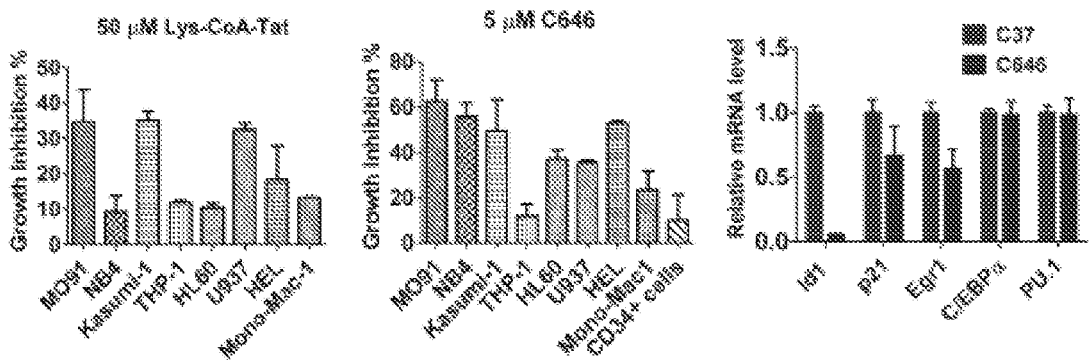

To understand how the NHR1 region affects transcriptional activation, whether A-E could directly bind p300 was examined. Baculovirus-expressed A-E and p300 directly interact in vitro (FIG. 10B), and an anti-ETO antibody co-immunoprecipitated the endogenous A-E and p300 proteins in Kasumi-1 cells, which do not express ETO (FIG. 10B). Several A-E or ETO deletion mutants were generated in order to map the p300 binding domain in A-E (FIGS. 2D and 4B). Both A-E and ETO bound p300. While deletions of the NHR2 domain in either ETO or A-E had no effect on p300 binding, deletion of the NHR1 domain (aa245-436) completely abrogated this binding (FIGS. 2D and 4B). Furthermore, the A-E exon 9a protein, an alternatively spliced form of A-E that lacks NHR3 and NHR4 (depicted in FIG. 5A), also interacts with p300 (FIG. 4B). Given that ETO can bind both co-repressor molecules and p300, ETO may function as a fast-response adaptor protein, inducing transcriptional activation or repression depending on the signaling pathways activated in the cell.

Figure 6:
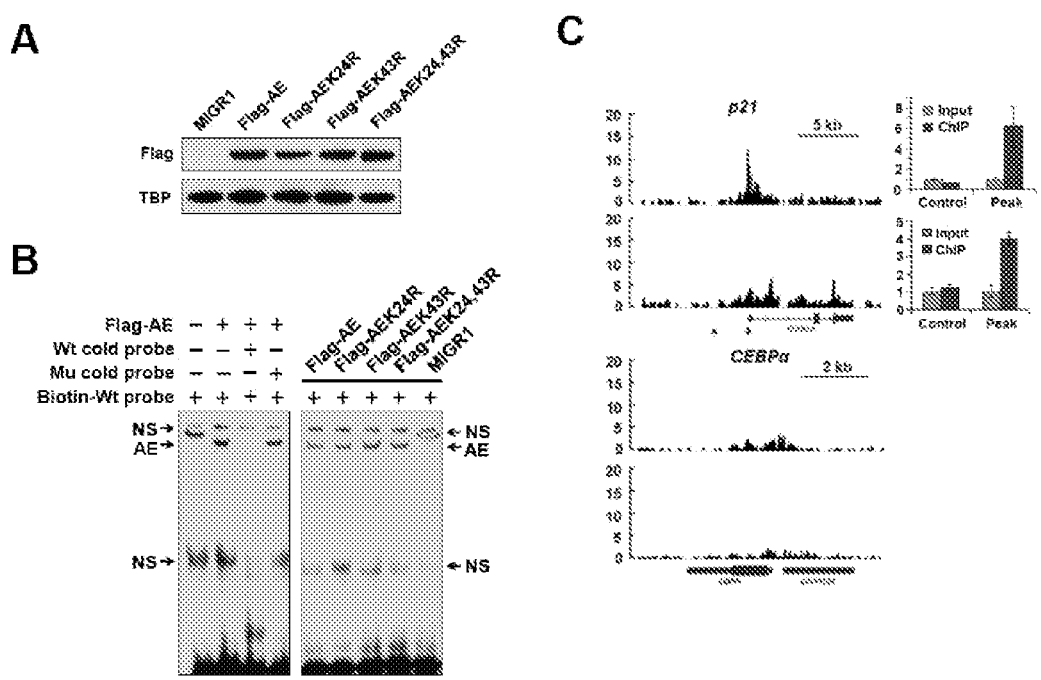
FIGS. 6A-6C show mutation of K43 to R in AML1-ETO does not affect its DNA binding ability. (A) Expression levels of AE, AEK24R, AEK43R or AEK24, 43R in nuclear extracts prepared from 293T cells, transfected with empty vector MIGR1, Flag-AE, FlagAEK24R, Flag-AEK43R or Flag-AEK24, 43R are shown. An anti-Flag antibody and anti-TBP antibody were used for Western blotting. (B) EMSA was performed using a biotin-labeled wild type (Wt) human Seperase probe containing two AML1 consensus binding sites. Wt cold human Seperase probe and mutant (Mu) cold Seperase probe containing the mutation in the second AML1 consensus site were used as competitors, to demonstrate sequence specific binding (shown on left). Nuclear extracts used in the EMSA are those shown in FIG. 6A. (C) AML1-ETO and p300 co-localize to some target genes activated by AML1-ETO. ChIP-seq was performed using Kasumi-1 cells and antibodies against ETO or p300. Co-occupancy of AML1-ETO and p300 on the p21 promoter but not the c/EBPα promoter is shown (as custom tracks in the UCSC genome browser). Binding of immunoprecipitated protein to a specific site results in a "peak"; the y-axis indicates number of tags aligned at each position in the genome. DNA binding was also analyzed by Q-PCR amplification of regions indicated by arrows on the x axis (±SD; n=3).

To determine whether p300 is important for the upregulated A-E target gene expression, p300 was knocked down in Kasumi-1 cells using two different shRNAs. Significant decreases were found in the levels of Id1, p21 and Egr1 mRNA, but no change in the levels of c/EBPα or PU.1 mRNA (FIG. 4C). The results presented herein indicate that p300 is essential for A-E mediated transcriptional activation. To further identify genes potentially regulated by A-E and p300, ChIP-seq (chromatin immunoprecipitation sequencing) assays were performed using anti-p300 and anti-ETO antibodies and the A-E expressing Kasumi-1 cells. It was found that the promoters of the Id1, p21 and Egr1 genes (genes activated by A-E) were co-occupied by A-E and p300 (FIGS. 4D and 6C). In contrast, p300 did not co-localize with A-E at the promoter (or enhancer) of the c/EBPα gene, which is repressed by A-E (FIGS. 4D and 6C). The results presented herein suggest p300 can contribute to the ability of A-E to function as a transcriptional activator and both can target similar transcriptional regulatory regions.

Figure 5:
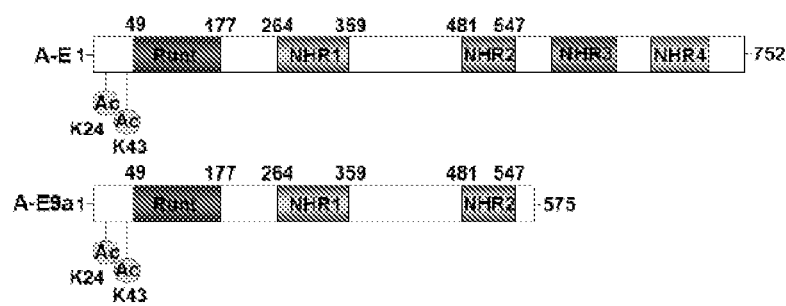
FIGS. 5A-5B show depictions of acetylation sites and known domains in AML1-ETO and AML1-ETO9a and conservation of K24 and K43 residues in AML1 of various species. (A) The AML1-ETO fusion protein includes Runt, NHR1, NHR2, NHR3 and NHR4 domains. The AML1 portion of AML1-ETO (aa 1 to 177) contains the Runt domain (aa 49 to 177), while the NHR1 (aa 264 to 359) and NHR2 (aa 481 to 547) domains are in the ETO portion. The AML1-ETO9a protein (which includes 575 amino acids) does not contain the NHR3 or NHR4 domains. (B) Alignment of N-terminal regions of AML1 from human, monkey, rat, mouse, chicken, xenopus and zebrafish.
Figure 7:
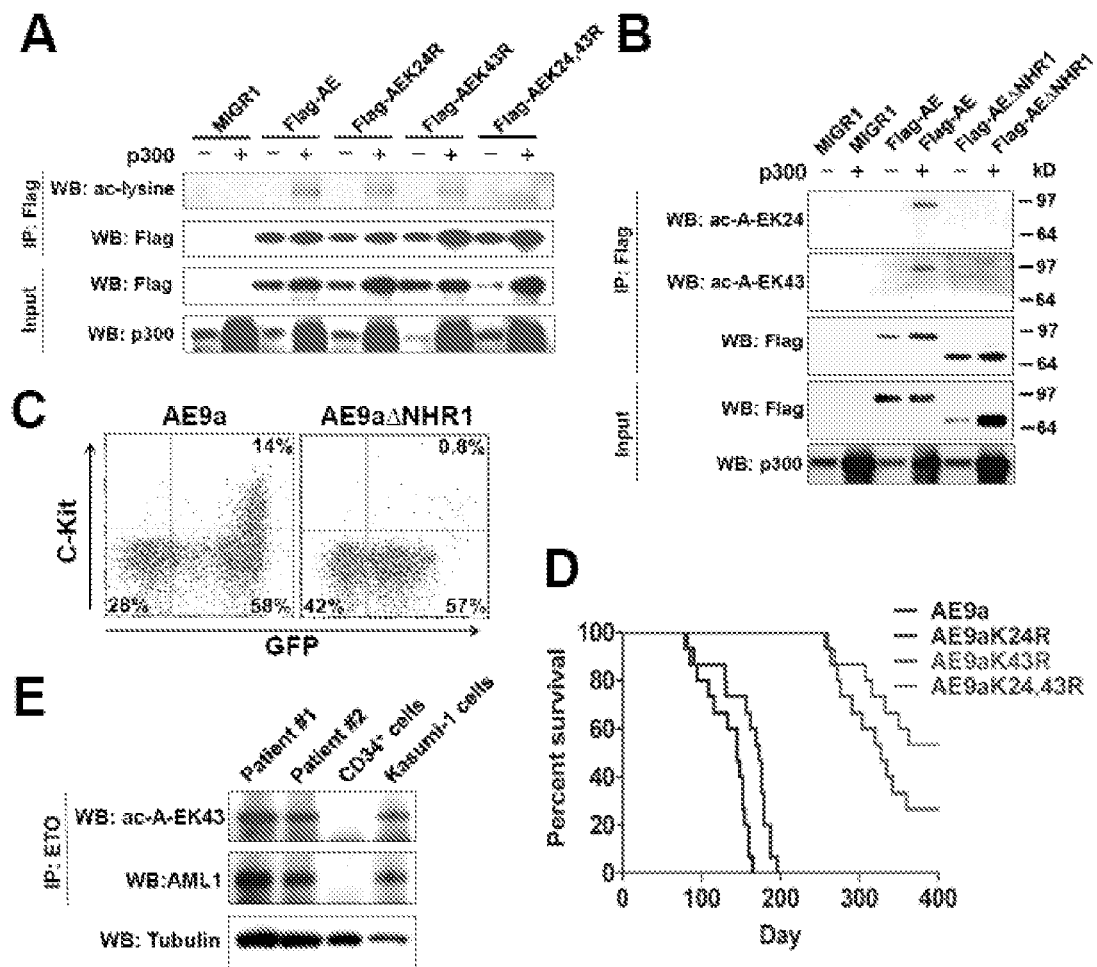
FIGS. 7A-7E show acetylation of A-EK43 by p300 is required for A-E induced transcriptional activation and leukemogenesis. (A) Acetylation of Flag-tagged A-E by p300. An anti-Flag or anti-acetyl lysine antibody was used for IP or for Western blotting. (B) Ability of A-E to bind p300 is required for its lysine acetylation. Anti-Flag antibody or anti-acetyl A-EK24 or K43 antibodies were used for IP or Western blotting (C) Lethally irradiated recipient mice were injected with HSPCs transduced with AE9a or AE9aΔNHR1. Number of GFP$^+$ C-Kit$^+$ cells in the peripheral blood (PB) is shown 15 weeks post-transplant. (D) Survival of mice receiving AE9a or AE9a mutants transduced HSPCs is shown (P<0.0001, n=15/group). (E) Acetylation of A-EK43 was detected in blast cells from t(8;21)$^+$ leukemia patients. Anti-ETO, acetyl A-EK43 or AML1 antibodies were used for IP or Western blotting (Zhao, X. et al, Genes Dev 22, 640, 2008).

Given that p300 acetylates a variety of protein targets, whether A-E is acetylated by p300 was examined, first by overexpressing A-E and p300 in 293T cells. A-E, but not ETO, is acetylated by p300, localizing the potential acetylation sites to the AML1 portion of A-E (aa 1 to 177) (FIG. 2E). Deletion of the Runt domain (aa 49 to 177) did not affect A-E acetylation (FIG. 2E), leaving K24 and K43 as the only candidate acetylation sites (FIG. 5A). K24 and K43 were mutated to arginine (R), separately and together, and it was confirmed that both K24 and K43 are acetylated by p300 using an anti-acetyl lysine antibody (FIG. 7A). Acetylation of K43 is abrogated following deletion of the NHR1 domain (245 to 436aa), the region responsible for the A-E/p300 interaction (FIG. 7B). The K24 and K43 residues are highly conserved in other vertebrates (FIG. 5B), which suggests that their acetylation may be conserved throughout evolution.

To define how acetylation of A-E affects its functions, the effects of "wild type" A-E with the A-EK24R, K43R and K24R/K43R mutant proteins on the in vitro behavior of transduced human HSPCs were compared (FIG. 3A). Like A-E, A-EK24R increased the number of CAFC present at week 5, while A-EK43R (and A-EK24R/K43R) did not (FIG. 3B and C). The K43 to R mutation also abrogated the effect of A-E on self-renewal, while the A-EK24R mutant protein retained this effect (FIG. 3D). The results presented herein suggest acetylation of AE at K43 is essential for its self-renewal promoting effects in human HSPCs (and for its effects on the self-renewal promoting genes Id1, p21 and Egr1, FIG. 3E).

Figure 8:
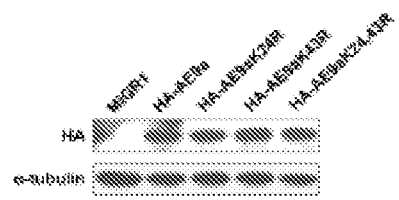
FIGS. 8A-8E show mutation of K43 to R in AML1-ETO9a blocks leukemia induction. (A) Mutation of K24R, K43R or K24, 43R in AE9a does not affect its expression level in mouse fetal liver LSK$^+$ cells. Mouse fetal liver LSK$^+$ cells transduced with MIGR1 empty vector, HA-AE9a, HA-AE9aK24R, HA-AE9aK43R or HA-AE9aK24,43R were analyzed. An anti-HA antibody and anti-tubulin antibody were used for Western blotting. (B) White blood counts (WBC) of AE9a (and AE9aK24R) groups are significantly higher than AE9aK43R or AE9aK24,43R groups, while red blood count (RBC) and platelet count (PLT) are lower (±SD; n=5). (C) FACS analysis showed that GFP$^+$ peripheral blood (PB) cells in AE9aK43R and AE9aK24, 43R groups express less C-kit compared to AE9a and AE9aK24R groups. AE9a (and AE9aK24R) GFP$^+$ PB cells lose CD45.2 and CD45 expression. (D) Morphology of bone marrow (BM), spleen and PB show lack of AML cells in K43R and K24, 43R groups (scale bars of BM and spleen samples: 10 µM; scale bars of PB samples: 25 µM). (E) AML1-ETO9a is acetylated at K43 in leukemia cells isolated from spleens of "AE9a mice".
Figure 8:
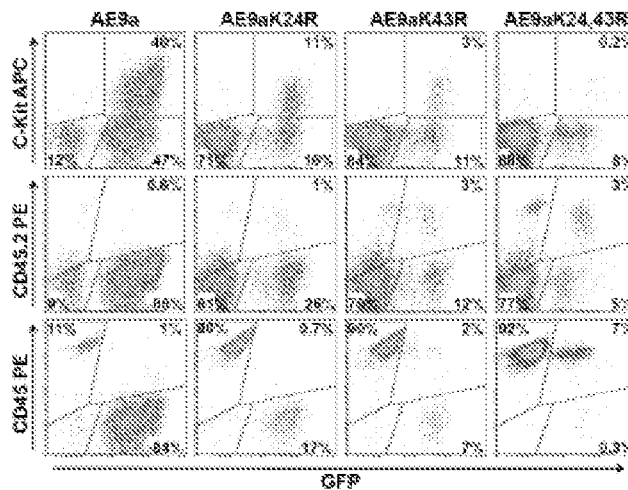
Figure 8:
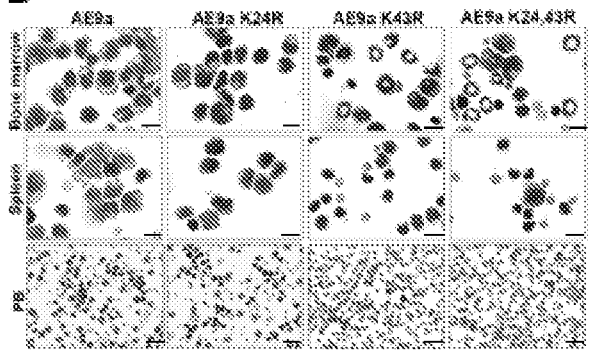
Figure 8:
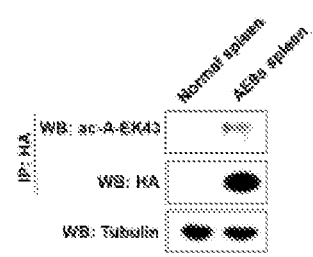

To investigate the role of A-E acetylation in in vivo leukemogenesis, wild type, K24R, K43R and K24R/K43R mutant forms of the AE9a protein (the isoform of A-E that can induce leukemia in mouse models by itself) were expressed in fetal liver HSPCs using retroviral transduction and transplantation assays (Yan, M. et al, *Nat Med* 12, 945, 2006). The peripheral blood, bone marrow, and spleen of the mice 15 weeks after transplantation was examined, and large numbers of blast cells were found in AE9a and AE9aK24R mice, but not in AE9aK43R or AE9aK24,43R mice (FIG. 8E). The AE9aK43R mice also had normal WBC counts, platelet counts and less anemia than the AE9a mice (FIG. 8C), while the blood counts of the AE9aK24R mice were as abnormal as those of the AE9a mice. The AE9aK43R mice also had far fewer C-kit$^+$ immature peripheral blood cells at 15 weeks than the AE9a mice or the AE9aK24R mice, and the cells retained expression of CD45 (FIG. 8D). All of the mice that received AE9a-transduced HSPCs developed AML; the median survival of the AE9a mice and the AE9aK24R mice was 145 and 173 days, respectively ($p<0.001$). However, the median survival of the AE9aK43R and AE9aK24,43R mice was 328 days and "not reached", respectively (FIG. 7D). Note that A-E9a is also acetylated on K43 in vivo, based on the AML cells isolated from the spleens of fully leukemic mice (FIG. 8E).

Since the NHR1 domain is required for the acetylation of A-EK43, whether its deletion affected the leukemogenicity of AE9a was examined. At 15 weeks post transplantation, the AE9aΔNHR1 mice had normal WBC counts and less anemia than the AE9a mice (FIG. 2F). The AE9aΔNHR1 mice also had far fewer GFP$^+$C-kit$^+$ immature cells in the peripheral blood than the AE9a mice at 15 weeks (0.8% vs 14%) (FIG. 7C). This in vivo result does differ from what has been reported using smaller NHR1 domain deletions, perhaps reflecting the size of the deletion or the use of different model systems (Yan, M. et al, *Blood* 113, 883, 2009; Kwok, C. et al, *Proc Natl Acad Sci USA* 106, 2853, 2009; Mannari, D. et al, *Leukemia*. 24, 891, 2010; Park, S. et al, *Blood*. 113, 3558, 2009).

Taken together, the results presented herein indicate that acetylation of AE9a at K43 is required for AE9a-induced leukemogenesis in mice. Of note, A-E, A-EK24R, A-EK43R and AEK24,43R are expressed at similar levels in the bone marrow cells (FIG. 6A) and they have similar DNA binding activity in electrophoretic mobility shift assays (FIG. 6B) (Okumura, A. J. et al, *Blood*. 112, 1392, 2008). To determine if A-E is acetylated in t(8;21) leukemia patient samples, two A-E-positive patient samples were analyzed. Detectable A-EK24 and K43 acetylation was found in both (FIGS. 3G and 7E).

Figure 9:
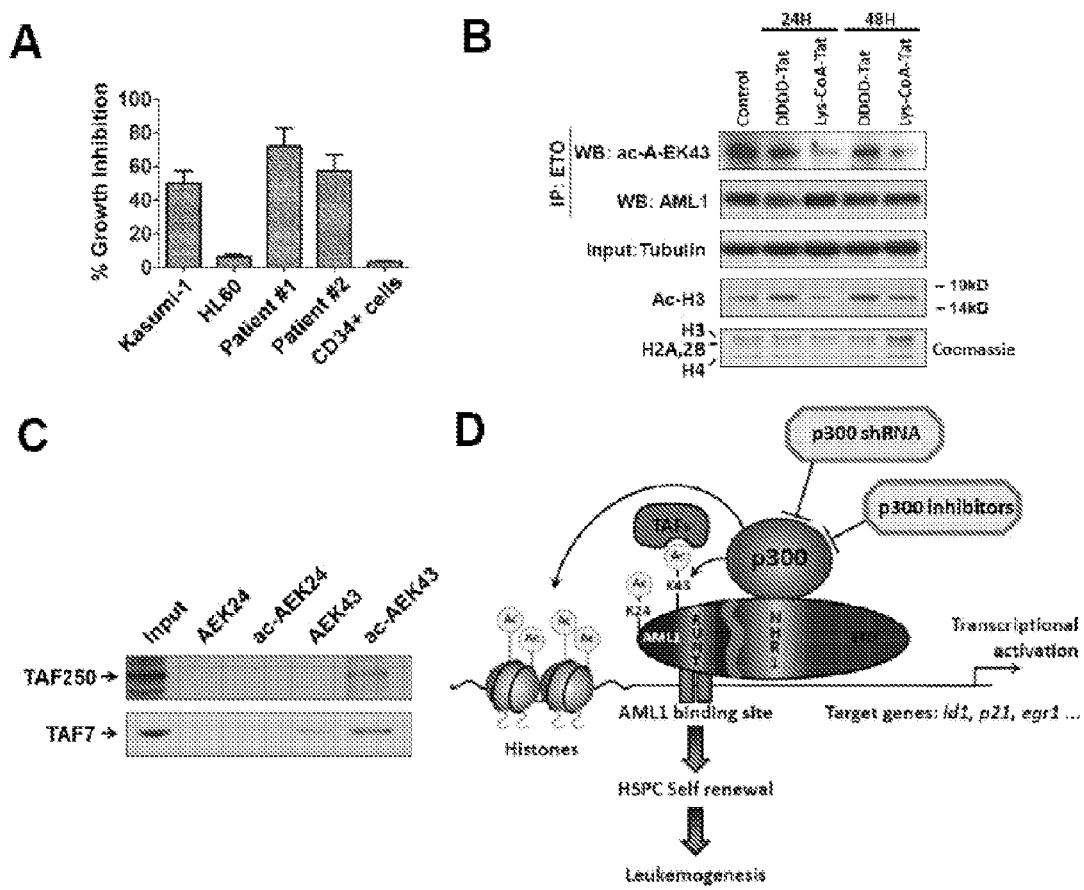
FIGS. 9A-9D shows inhibition of p300 or lysine acetylation blocks leukemogenesis by inducing apoptosis and downregulating expression of AML1-ETO activated target genes. (A) Lys-CoA-Tat (50 µM) but not DDDD-Tat inhibited growth of primary t(8;21)$^+$ leukemia cells and Kasumi-1 cells (±SD; n=3). (B) Lys-CoA-Tat (50 µM) blocks A-EK43 and histone H3 acetylation in Kasumi-1 cells, as detected by anti-acetyl A-EK43 or histone H3 antibodies. (C) Binding of TAF250 and TAF7 to A-E peptides that contain acetylated or unacetylated K24 or K43 was studied using a peptide pull-down assay. Antibodies against TAF250 or TAF7 were used for Western blotting. (D) A schematic model showing how p300, and acetylation of A-E by p300, cooperate to induce leukemia.

To define whether acetylation of A-E is required to inhibit differentiation, the level of Glycophorin A and CD11b expression on transduced cells grown in differentiation-driving cytokines was examined. Both A-E and A-EK24R/K43R triggered a similar decrease in the expression of these differentiation markers (FIG. 3F). The results presented herein suggest the absence of A-EK43 acetylation affects the self-renewal signals provided by A-E, but not the delay/block in differentiation, which is consistent with its effects on the myeloid differentiation genes c/EBPα and PU.1 (FIG. 3E). Mass spectrometry was performed and it was found that a K43 acetylated-A-E peptide (but not the non-acetylated peptide) preferentially bound a variety of proteins, including several components of the transcriptional pre-initiation complex (TAFs). A peptide pull-down assay was performed, and binding was found to both TAF7, and TAFII250 (FIG. 9C). This result described herein suggests that the acetylation of A-EK43, which is critical for A-E induced transcriptional activation, may work at least in part, by promoting the recruitment of bromodomain containing TAF proteins. Of course HATs other than p300 may also contribute to the acetylation of A-E, and the K43 containing region may recruit transcription factors, or other co-activators in addition to bromodomain containing proteins.

Given the importance of the interaction of A-E with p300, and its subsequent acetylation, whether inhibiting p300 function, using RNAi or chemical inhibitors, would alter leukemia cell growth was assessed. Knock down of p300 decreased the level of A-E acetylation (FIG. 10A) and decreased the expression of Id1, p21 and Egr1 (FIG. 4C). Primary t(8;20$^+$ leukemia cells, isolated from patients, and t(8;21)$^+$ Kasumi-1 cells were also treated with the p300 inhibitor Lys-CoA-Tat and a second p300 inhibitor C646 (Liu, X. et al. *Nature* 451, 846, 2008; Bowers, E. M., et al. *Chemistry & Biology* 17, 471, 2010). Both inhibitors decreased the level of Id1, p21 and Egr1 mRNA, and the level of acetylated A-EK43 and histone H3 (FIGS. 9B and 10A). Lys-CoA-Tat also inhibited the growth of the t(8;21) positive primary patient leukemia cells and Kasumi-1 cells (as did C646), with little effect on the growth of normal human HSPCs (FIGS. 9A and 10C). Furthermore, both Lys-CoA-Tat and C646 inhibited the growth of MO-91, U937, NB4 and HEL cells at 5 µM, with minimal effect on THP-1, Mono-Mac-1 or HL60 cells (FIG. 10C). The results presented herein suggest other acetylated proteins, such as the non-histone substrates of p300, may regulate the sensitivity of cells to p300 inhibition suggesting that inhibition of p300 function could have broader therapeutic potential in AML.

Figure 11:
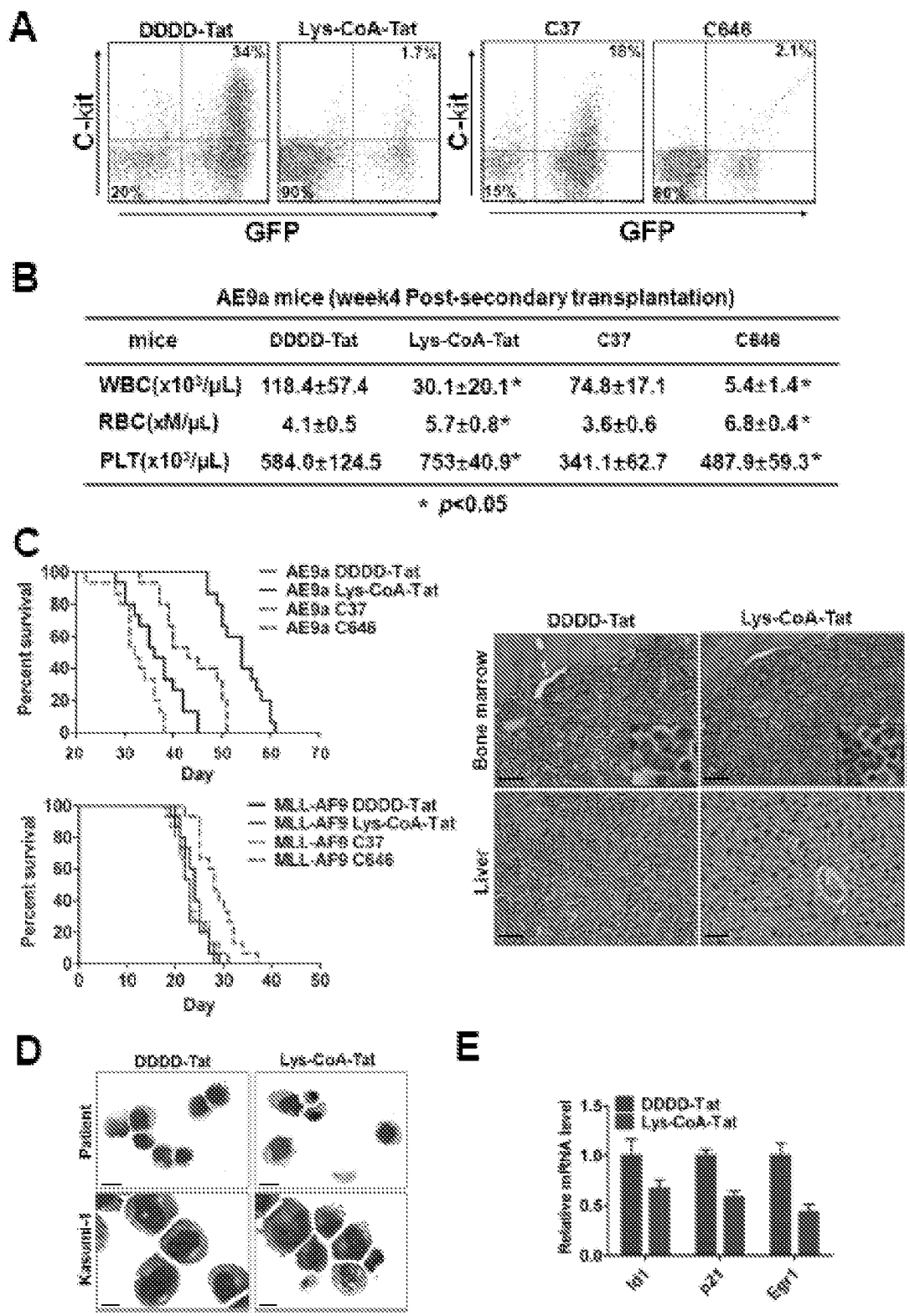
FIGS. 11A-E show effects of p300 inhibitors on AE9a mouse AML models. (A) Percent of GFP$^+$ C-Kit$^+$ cells in peripheral blood of mice that received Lys-CoA-Tat or C646 treated AE9a leukemia cells was significantly less than mice that received DDDD-Tat or C37 treated cells. (B) WBC counts of mice that received Lys-CoA-Tat or C646 treated AE9a cells were significantly lower than mice that received DDDD-Tat or C37 treated cells, while red blood cell count (RBC) and platelet count (PLT) of Lys-CoA-Tat or C646 treated group were higher (±SD; n=5). (C) Effect of p300 inhibitor treatment on survival of AE9a mice and MLL-AF9 mice. AE9a or MLL-AF9 expressing mouse leukemia cells were treated with 50 µM Lys-CoA-Tat (DDDD-Tat as control) or 20 µM C646 (C37 as control) for 12 hours ex vivo, and injected into recipient mice that had received a sublethal dose of irradiation. Each group included 15 mice, and overall survival times are shown (left panel). Median survival of AE9a mice was extended from 36 to 54 days by DDDD-Tat vs Lys-CoA-Tat treatment, and from 32 to 43 days by C37 vs C646 treatment (p<0.0001). Median survival of MLL-AF9 mice was not extended by Lys-CoA-Tat treatment (24 days vs 23 days for DDDD-Tat) but was slightly prolonged by C646 treatment (28 days vs 23 days for C37). BM and liver pathological sections, stained with hematoxylin-eosin (HE), are shown in right panels (scale bar: 25 µM). (D) The p300 inhibitor, Lys-CoA-Tat, induced apoptosis of primary leukemia cells isolated from patients with t(8;21) leukemia, as well as Kasumi-1 cells. Apoptotic cells were identified by morphological analysis (scale bar: 10 µM). (E) Lys-CoA-Tat downregulated expression of AML1-ETO activated target genes at 24 hours. Kasumi-1 cells were treated with 50 µM Lys-CoA-Tat for 24 hours, and RNA was collected to measure Id1, p21 and Egr1 mRNA levels by qPCR (±SD; n=3).

The effect of p300 inhibitors on leukemia cell growth in vivo was examined using two different mouse leukemia models. 3×10$^6$ AE9a or MLL-AF9 expressing leukemia cells were treated ex vivo with Lys-CoA-Tat or C646 for 12 hours before injecting the cells into sublethally irradiated C57Bl/6 mice (Day 0) (Wang, L. et al, *Cell Death Differ* 14, 306, 2007). Both p300 inhibitors reduced the number of immature GFP$^+$C-kit$^+$ cells in the AE9a mice (FIG. 11A) leading to lower white blood counts, less anemia and less thrombocytopenia, compared to the recipients of DDDD-Tat or C37 treated AE9a cells (FIG. 11B). These p300 inhibitors significantly increased the median survival from 36 days to 54 days for Lys-CoA-Tat and from 32 days to 43 days for C646, p<0.0001 (FIG. 11C). In contrast, Lys-CoA-Tat did not affect the survival of the MLL-AF9 leukemia mice, and C646 had only a minimal effect on MLL-AF9 driven leukemia, increasing the median survival from 23 days to 28 days (FIG. 11C). The results presented herein suggest p300 inhibitors can block the transcriptional activating function of A-E, and decrease the growth of A-E expressing leukemia cells, providing a new, potentially therapeutic approach to t(8;21) AML (and possibly other AML subtypes as well).

CONCLUSION

In summary, the results presented herein demonstrate that acetylation of A-E (and AE9a) by p300 is required for their leukemogenic effects in a human preleukemia model and a mouse AML model. The NHR1 domain of A-E provides a docking site for p300, allowing A-E and p300 to co-localize at the regulatory regions of many A-E upregulated genes, including those involved in self-renewal (e.g., Id1, p21 and Egr1). The critical consequence of this interaction is that A-E is acetylated, an event essential for its self-renewal promoting effects and its ability to activate gene expression. Thus, even though A-E can bind p300 and presumably bring it to chromatin where it can acetylate histone residues, it is the acetylation of A-E itself that is the key step, perhaps at least in part by recruiting bromodomain containing proteins such as TAFII250 or TAF7 (see our model for A-E induced leukemogenesis in FIG. 9D). The finding presented herein that the site-specific lysine acetylation of the AML1-ETO oncogenic fusion protein contributes potently to leukemogenesis, suggests that inhibiting its acetylation could represent a promising therapeutic strategy for t(8;21)$^+$ leukemia.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. A method of identifying agents for treating or reducing risk for acute myelogenous leukemia comprising:

providing a system comprising at least AML1-ETO and p300, in which AML1-ETO acetylation level is determinable;

contacting the system with a test agent;

determining AML1-ETO acetylation level when the test agent is present;

comparing the determined AML1-ETO acetylation level with a reference AML1-ETO acetylation level so that any difference between the reference level and the determined level is detected; and characterizing the test agent's usefulness in treating or reducing risk for acute myelogenous leukemia based on the detected difference.

2. The method of claim 1, wherein the reference AML1-ETO acetylation level is that observed in the system under comparable conditions lacking the test agent.

3. The method of claim 1, wherein the reference AML1-ETO acetylation level is that observed in the system under otherwise identical conditions lacking the test agent.

4. The method of claim 1, wherein the reference AML1-ETO acetylation level is that observed in the system under comparable conditions that include presence of a positive control agent.

5. The method of claim 1, wherein the reference AML1-ETO acetylation level is that observed in the system under comparable conditions that include presence of a negative control agent.

6. The method of claim 1, wherein the reference AML1-ETO acetylation level is that observed in a comparable system under comparable conditions lacking the test agent.

7. The method of claim 1, wherein the reference AML1-ETO acetylation level is that observed in a comparable system under otherwise identical conditions lacking the test agent.

8. The method of claim 1, wherein the reference AML1-ETO acetylation level is that observed in a comparable system under comparable conditions that include presence of a positive control agent.

9. The method of claim 1, wherein the reference AML1-ETO acetylation level is that observed in a comparable system under comparable conditions that include presence of a negative control agent.

10. The method of claim 1, wherein the reference AML1-ETO acetylation level is a historical level.

11. The method of claim 1, wherein the system is an in vitro system.

12. The method of claim 11 wherein the in vitro system comprises cultured cells.

13. The method of claim 12 wherein the cultured cells comprise acute myelogenous leukemia cells.

14. The method of claim 12 wherein the cultured cells are transfected with a vector containing no insert or the vector containing AML1-ETO (SEQ ID NO.1).

15. The method of claim 1, wherein the system is an in vivo system.

16. The method of claim 15 wherein the in vivo system comprises mice expressing AML1-ETO (SEQ ID NO. 1).

17. The method of claim 1, wherein the acetylation level of AML1-ETO comprises acetylation on amino acid K43.

* * * * *

UNITED STATES PATENT AND TRADEMARK OFFICE
CERTIFICATE OF CORRECTION

| | | |
|---|---|---|
| PATENT NO. | : 9,435,809 B2 | |
| APPLICATION NO. | : 14/232801 | |
| DATED | : September 6, 2016 | |
| INVENTOR(S) | : Stephen D. Nimer and Lan Wang | |

It is certified that error appears in the above-identified patent and that said Letters Patent is hereby corrected as shown below:

In the Specification

In Column 1, beginning at Line 13 and ending at Line 18, please delete:

"The United States Government has provided grant support utilized in the development of the present invention. In particular, National Institutes of Health grant number GM62437 has supported development of this invention. The United States Government may have certain rights in the invention."

and insert:

-- This invention was made with government support under grant number GM062437 awarded by National Institutes of Health. The government has certain rights in the invention. --

Signed and Sealed this
Third Day of January, 2017

Michelle K. Lee
*Director of the United States Patent and Trademark Office*